(12) United States Patent
Dishler et al.

(10) Patent No.: US 11,547,552 B2
(45) Date of Patent: **\*Jan. 10, 2023**

(54) SMALL DIAMETER CORNEAL INLAYS

(71) Applicant: RVO 2.0, INC, Aliso Viejo, CA (US)

(72) Inventors: Jon Dishler, Greenwood Village, CO (US); Troy A. Miller, Centennial, CO (US); Alexander Vatz, Lake Winnebago, MO (US); James R. Alexander, Newport Beach, CA (US)

(73) Assignee: RVO 2.0, INC, Aliso Viejo, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/950,745

(22) Filed: Nov. 17, 2020

(65) Prior Publication Data

US 2021/0068943 A1    Mar. 11, 2021

Related U.S. Application Data

(63) Continuation of application No. 15/219,130, filed on Jul. 25, 2016, now Pat. No. 10,835,371, which is a continuation of application No. 13/854,588, filed on Apr. 1, 2013, now abandoned, which is a continuation of application No. 12/877,799, filed on Sep. 8, 2010, now abandoned, which is a continuation-in-part of application No. 12/418,325, filed on Apr. 3, 2009, now Pat. No. 8,900,296, which is a continuation-in-part of application No. 11/738,349, filed on Apr. 20, 2007, now abandoned, said application No. 12/877,799 is a continuation-in-part of application No. 11/554,544, filed on Oct. 30, 2006, now Pat. No. 8,057,541.

(60) Provisional application No. 60/776,458, filed on Feb. 24, 2006.

(51) Int. Cl.
*A61F 2/14* (2006.01)
*B29D 11/00* (2006.01)
*A61L 27/14* (2006.01)

(52) U.S. Cl.
CPC .............. *A61F 2/147* (2013.01); *A61F 2/145* (2013.01); *A61L 27/14* (2013.01); *B29D 11/00009* (2013.01)

(58) Field of Classification Search
CPC ................. A61L 27/14; A61L 2430/16; B29D 11/0009–11/00403; A61F 2/145–2/147; A61F 2240/001; A61F 2250/0091
See application file for complete search history.

(56) References Cited

U.S. PATENT DOCUMENTS

| 4,466,705 | A | * | 8/1984 | Michelson | G09B 23/30 351/159.33 |
| 5,336,261 | A | * | 8/1994 | Barrett | A61F 2/1451 623/5.11 |

(Continued)

*Primary Examiner* — Paul B Prebilic
(74) *Attorney, Agent, or Firm* — McCarter & English, LLP; Beverly W. Lubit

(57) ABSTRACT

Methods of manufacturing and implanting corneal inlays, such as small diameter corneal inlays, are provided. The methods include manufacturing an implant body to have a meniscus shape with a small diameter and an index of refraction, and implanting the implant body in a corneal bed of a cornea. The inlays cause a change in an anterior surface of the cornea after implantation due to the implant body.

3 Claims, 20 Drawing Sheets

(56) References Cited

U.S. PATENT DOCUMENTS 10,709,546 B2 * 7/2020 Peyman ................ A61F 2/1453
2003/0014042 A1 * 1/2003 Juhasz .................... A61F 2/147
606/166

* cited by examiner

SMALL DIAMETER CORNEAL INLAYS

CROSS-REFERENCE TO RELATED APPLICATIONS

This application is a continuation of U.S. application Ser. No. 15/219,130, filed Jul. 25, 2016, now U.S. Pat. No. 10,835,371, which application is a continuation of U.S. application Ser. No. 13/854,588, filed Apr. 1, 2013, now abandoned; which application is a continuation of U.S. application Ser. No. 12/877,799, filed Sep. 8, 2010, now abandoned; which application is a continuation-in-part of U.S. application Ser. No. 11/554,544, filed Oct. 30, 2006, now U.S. Pat. No. 8,057,541, which claims the benefit of Provisional Appln. No. 60/776,458, filed Feb. 24, 2006;

U.S. application Ser. No. 12/877,799, filed Sep. 8, 2010, is also a continuation-in-part of U.S. application Ser. No. 12/418,325, filed Apr. 3, 2009, now U.S. Pat. No. 8,900,296; which is a continuation-in-part of U.S. application Ser. No. 11/738,349, filed Apr. 20, 2007, now abandoned.

All of the aforementioned applications are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Abnormalities in the human eye can lead to vision impairment. Some typical abnormalities include variations in the shape of the eye, which can lead to myopia (near-sightedness), hyperopia (far-sightedness) and astigmatism as well as variations in the tissue present throughout the eye, such as a reduction in the elasticity of the lens, which can lead to presbyopia. A variety of technologies have been developed to try and address these abnormalities, including corneal implants.

Corneal implants can correct vision impairment by altering the shape of the cornea. Corneal implants can be classified as an onlay or an inlay. An onlay is generally considered an implant that is placed over the cornea such that the outer layer of the cornea, e.g., the epithelium, can grow over and encompass the implant. An inlay is generally considered an implant that is implanted in the cornea beneath a portion of the corneal tissue by, for example, cutting a flap in the cornea and inserting the inlay beneath the flap. Because the cornea is the strongest refracting optical element in the human ocular system, altering the cornea's anterior surface is a particularly useful method for correcting vision impairments caused by refractive errors. Inlays are also useful for correcting other visual impairments including presbyopia.

SUMMARY OF THE INVENTION

The disclosure generally describes corneal inlays which are adapted to change the shape of the cornea to provide central near vision zone and a peripheral distance vision zone in the cornea. In general, the inlay is sized such that when positioned within the cornea, a central region of the cornea increases in curvature, thereby providing for near vision. A region peripheral to the central region provides for distance vision.

One aspect of the disclosure describes a corneal inlay comprising an inlay body having a diameter between about 1 mm and about 3 mm, wherein the body has an index of refraction that is substantially the same as a cornea. The inlay can have an index of refraction that is about 1.36 to about 1.39.

In some embodiments the diameter of the inlay is about 2 mm.

In some embodiments the inlay body has a central thickness that is about 20 microns to about 50 microns, and in some embodiments it is about 30 microns.

In some embodiments the inlay has a peripheral edge thickness between about 8 microns and about 15 microns, and in some embodiments is about 12 microns.

In some embodiments the inlay body has an anterior radius of curvature between about 7 mm and about 12 mm, and in some embodiments in about 10 mm.

In some embodiments the inlay body has a posterior radius of curvature between about 5 mm and about 10 mm, and in some embodiments is about 8.5 mm.

DETAILED DESCRIPTION OF THE INVENTION

Figure 1:
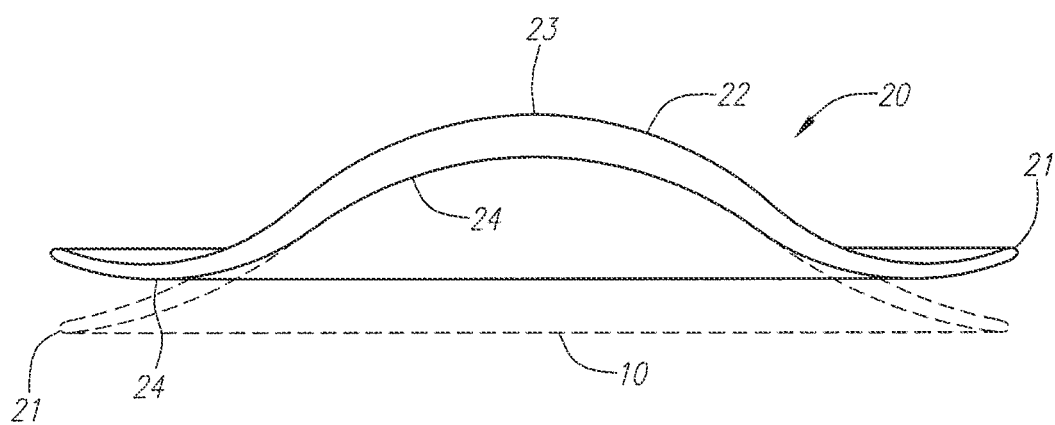
FIG. 1 is a cross-sectional view of a conventional implantable lens.

Some corneal implants that are relatively flat around the outer edges, such as aspherical implants and shallow spherical implants to name a few, can suffer from edge lift. Edge lift occurs when the anterior surface of the implant around the outer edge tends to curve or lift back towards the apex. FIG. 1 is a cross-sectional view of a conventional corneal implant 20 suffering from edge lift, which is exaggerated for the purposes of illustration. Here, the implant 20 has an outer edge 21, an anterior surface 22, an apex 23 and a posterior surface 24. An ideal edge profile is indicated by dashed line 10. In the ideal case, the most posterior point on the anterior surface 22 is located at the outer edge 21. However, in a lens suffering from edge lift the most posterior point of the anterior surface 22 can be located at a position 24 closer to the apex 23 than the outer edge 21. Edge lift can progress and build up over time and result in deteriorated optical performance and can also make the implantation procedure more difficult.

Figure 2A:
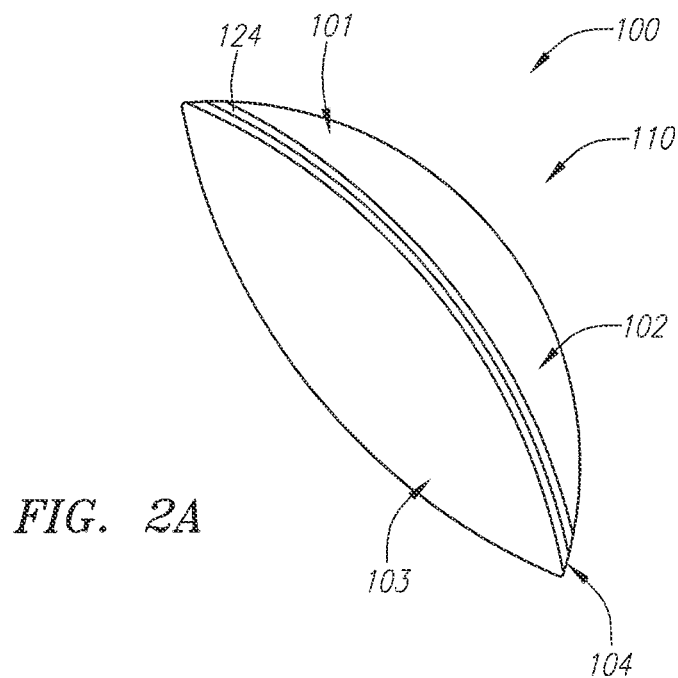
FIG. 2A is a perspective view depicting an example embodiment of an implantable lens.
Figure 2B:
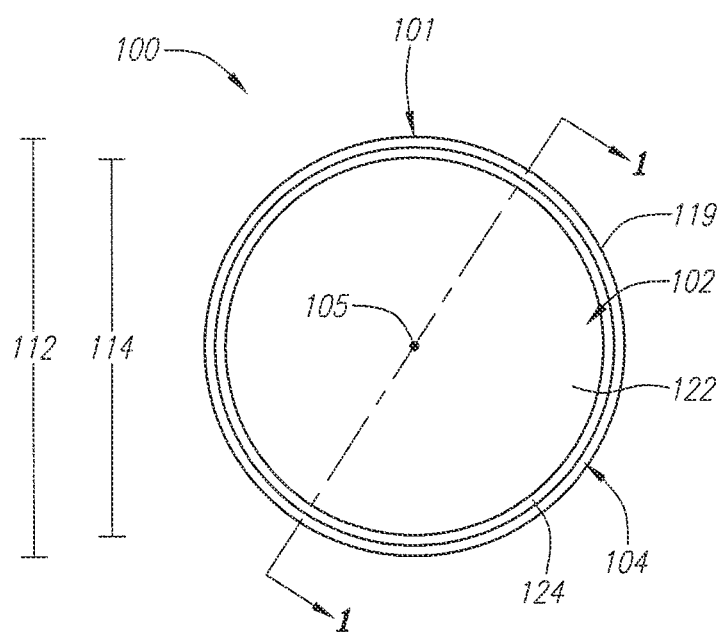
FIG. 2B is a top-down view depicting another example embodiment of the implantable lens.

In some embodiments the inlays have modified edge regions that can reduce stimulation of adverse tissue reactions in proximity to the lens. FIGS. 2A-E depict various views of an example embodiment of implantable lens 100. FIG. 2A is a perspective view depicting implantable lens 100, where lens 100 has lens body 101, anterior surface 102, posterior surface 103 and outer edge surface 104. FIG. 2B is a top-down view of lens 100 taken in direction 110. Here it can be seen that lens body 101 has a generally circular outer profile 119 with central apex 105 representing the most anterior point of anterior surface 102. Diameter 112 represents the overall diameter of lens body 101 and diameter 114 represents the diameter of corrective portion 122, which is the portion of anterior surface 102 configured to provide correction for one or more specific visual impairments.

Figure 2C:
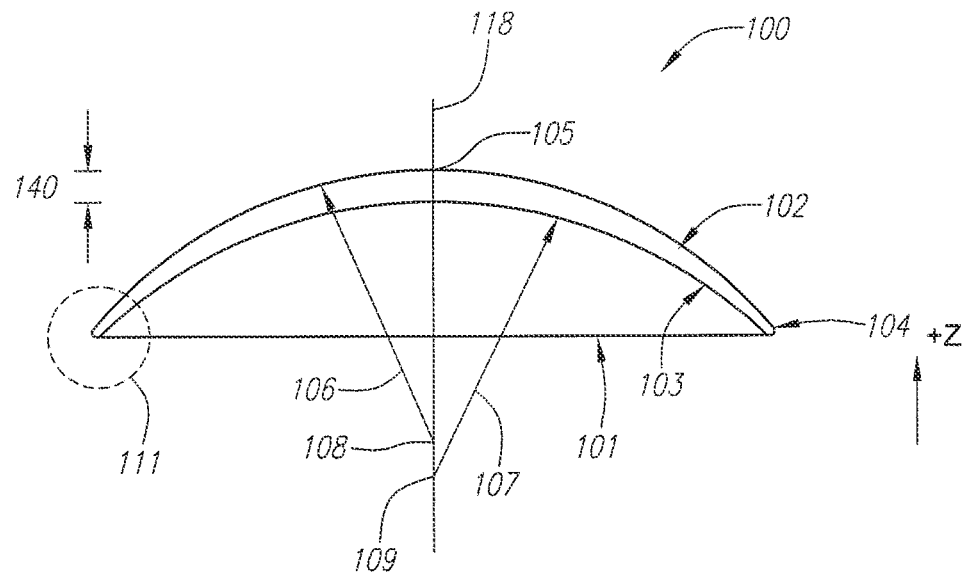
FIGS. 2C, 2D and 2E are cross-sectional views taken along line 1-1 of FIG. 2B depicting additional example embodiments of the implantable lens.

FIG. 2C is a cross-sectional view of lens 100 taken along line 1-1 of FIG. 2B. From this view it can be seen that anterior surface 102 is substantially spherical with radius of curvature 106 measured from vertex 108 located on central axis 118, which intersects apex 105. Likewise, posterior surface 103 also has its own radius of curvature 107 measured from vertex 109. The corrective power of lens 100 is dependent upon these radii 106-107 and can be varied as desired by adjustment of either radii 106-107. It can also be seen here that lens 100 is configured to correct for hyperopia, i.e., the relation of anterior surface 102 to posterior surface 103 gives lens body 101 a converging meniscus-like shape along line 1-1. The thickness of lens body 101 along central axis 118 is referenced as center thickness 140.

Figure 2D:
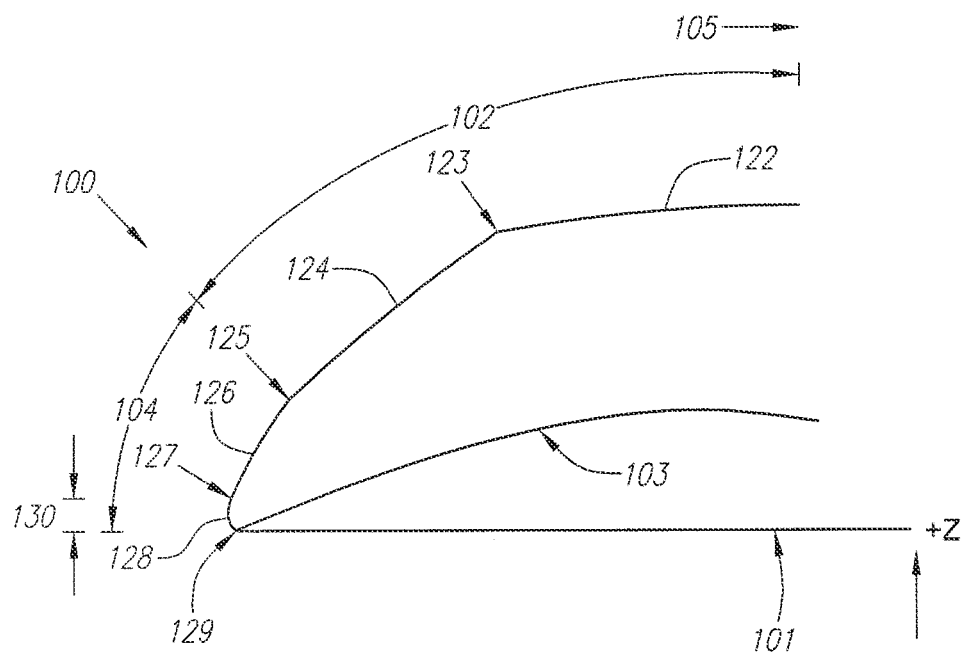

FIG. 2D is an enlarged cross-sectional view of lens 100, showing region 111 of FIG. 2C in greater detail. In FIG. 2D, corrective portion 122 of anterior surface 102 is substantially spherical and anterior surface 102 also includes a beveled portion 124. Here, beveled portion 124 is curved with a single radius of curvature and is referred to as bevel radius 124. As used herein, "bevel" is defined to include flat surfaces, curved surfaces and surfaces of any other shape. Bevel radius 124 abuts spherical portion 122 at interface 123. Adjacent to bevel radius 124 is outer edge surface 104, the abutment between bevel radius 124 and outer edge surface 104 being referenced as interface 125. Outer edge surface 104 includes first portion 126 and second portion 128, which abut each other at interface 127. Second edge surface portion 128 abuts posterior surface 103 at interface 129. Here, first edge surface portion 126 is curved and is referred to as edge radius 126. In this embodiment, edge thickness 130 is defined as the height of second edge surface portion 128 in the Z direction from the most posterior point of lens body 101 (interface 129 in this instance) to interface 127.

Figure 2E:
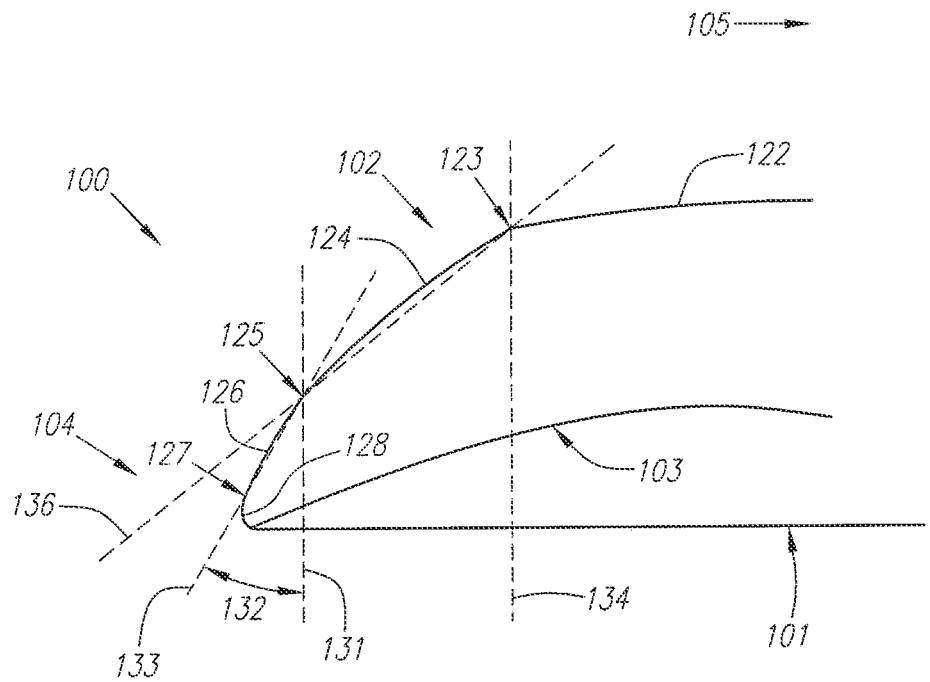

FIG. 2E is another cross-sectional view of region 111 depicting the example embodiment of FIG. 2D with edge radius slope angle 132, which defines the slope of edge radius 126. Edge radius slope angle 132 can be defined as the angle between axes 131 and 133. Here, axis 131 is parallel to central axis 118 and intersects interface 125, while axis 133 intersects interfaces 125 and 127. Also depicted here is bevel radius slope angle 135, which defines the slope of bevel radius 124. Bevel radius slope angle 135 can be defined as the angle between axes 134 and 136. Here, axis 134 is parallel to central axis 118 and intersects interface 123 and axis 136 intersects interfaces 123 and 125.

As can be seen in FIGS. 2D-E, edge radius 126 preferably slopes in the −Z direction to a greater degree than bevel radius 124, so that edge radius 126 converges towards posterior surface 103 at a greater rate than bevel radius 124. Stated in terms of slope angles, edge radius slope angle 132 is preferably smaller than bevel radius slope angle 135. As a result, lens 100 is less susceptible to edge lift. Also, the gradual transition between spherical portion 122 and posterior surface 103 can reduce stimulation of adverse tissue reactions to lens 100.

Figure 3:
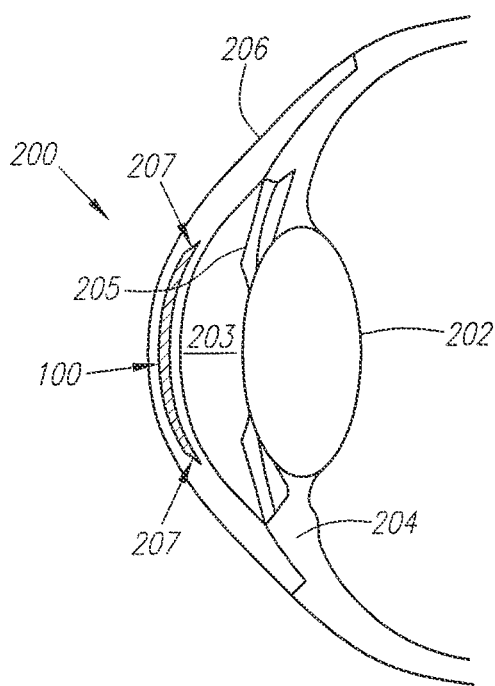
FIG. 3 is a cross-sectional view depicting an anterior portion of a human eye with an example embodiment of the lens implanted therein.
Figure 4:
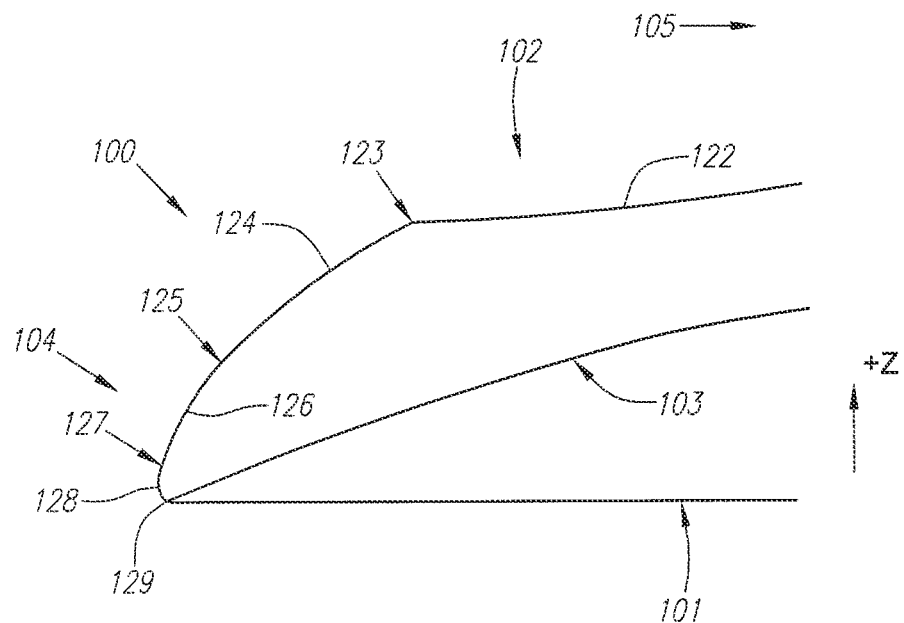
FIGS. 4, 5, 6, 7, 8 and 9 are cross-sectional views taken along line 1-1 of FIG. 1B depicting additional example embodiments of the implantable lens.
Figure 5:
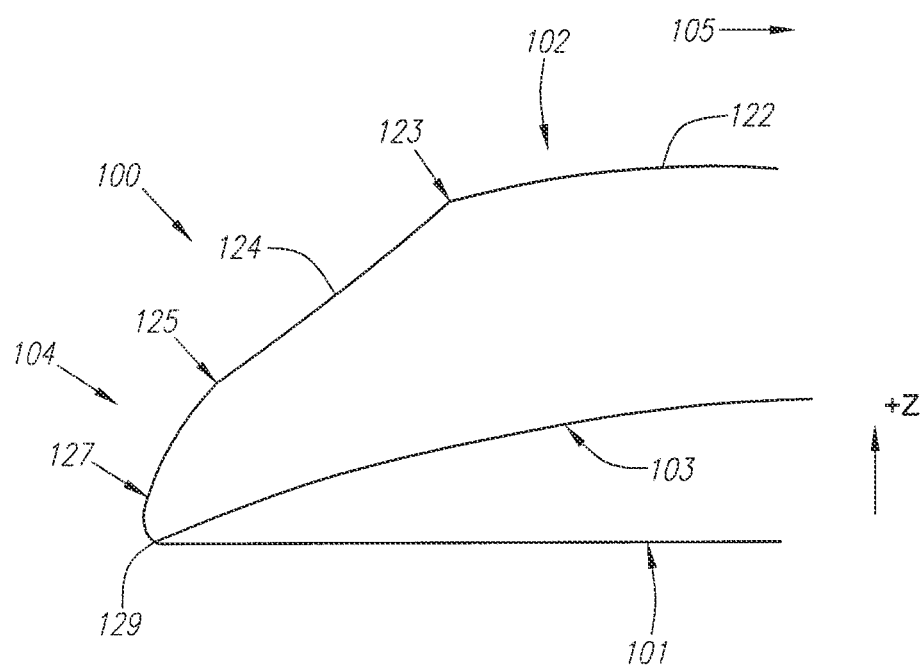
Figure 6:
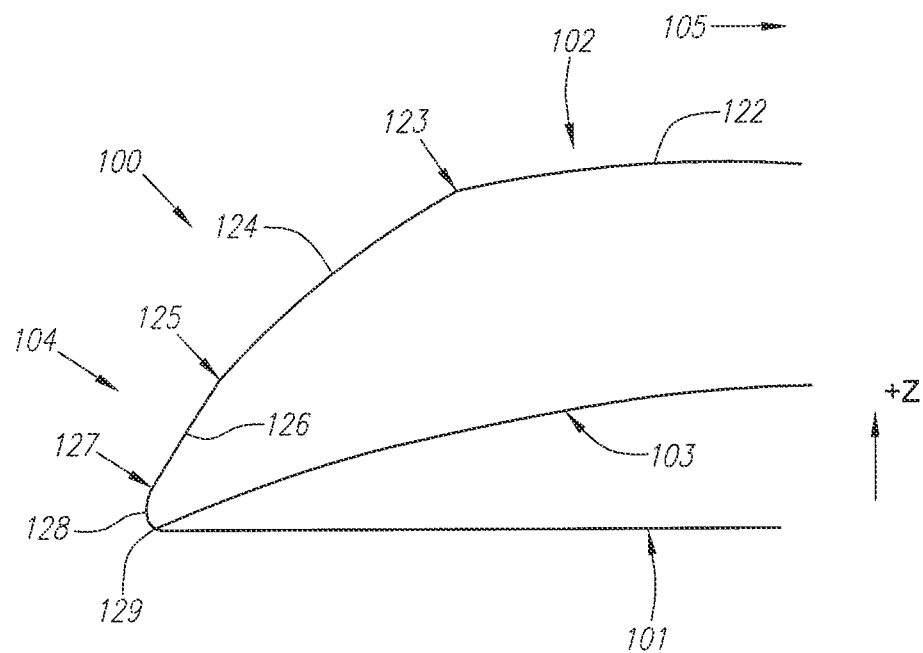
Figure 7:
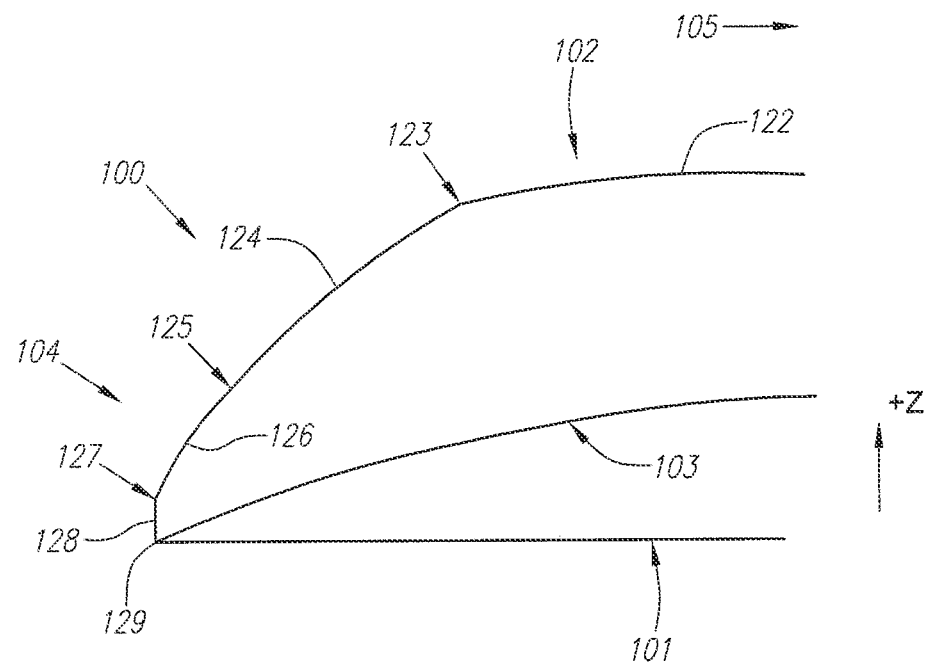
Figure 8:
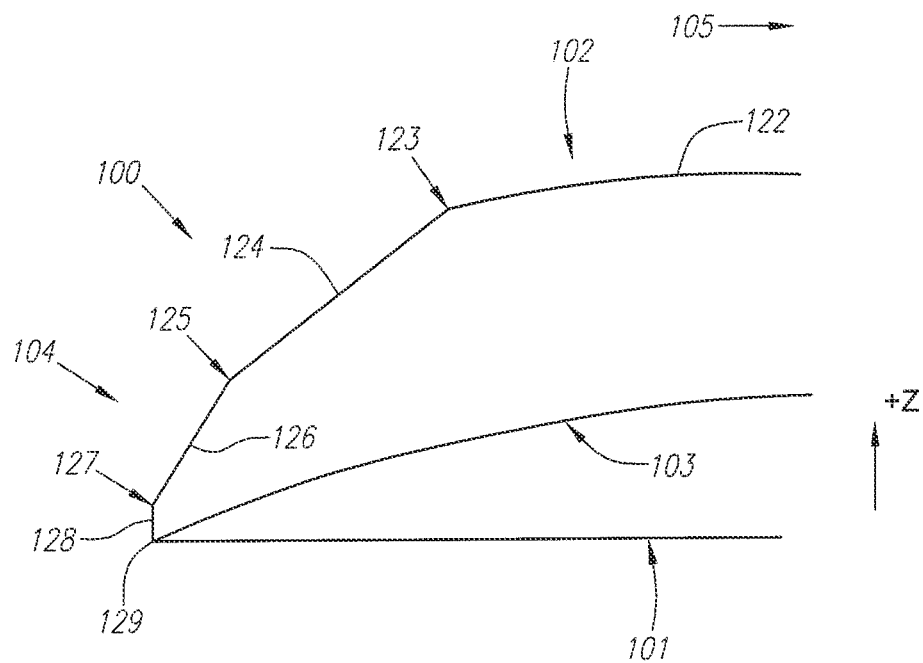
Figure 9:
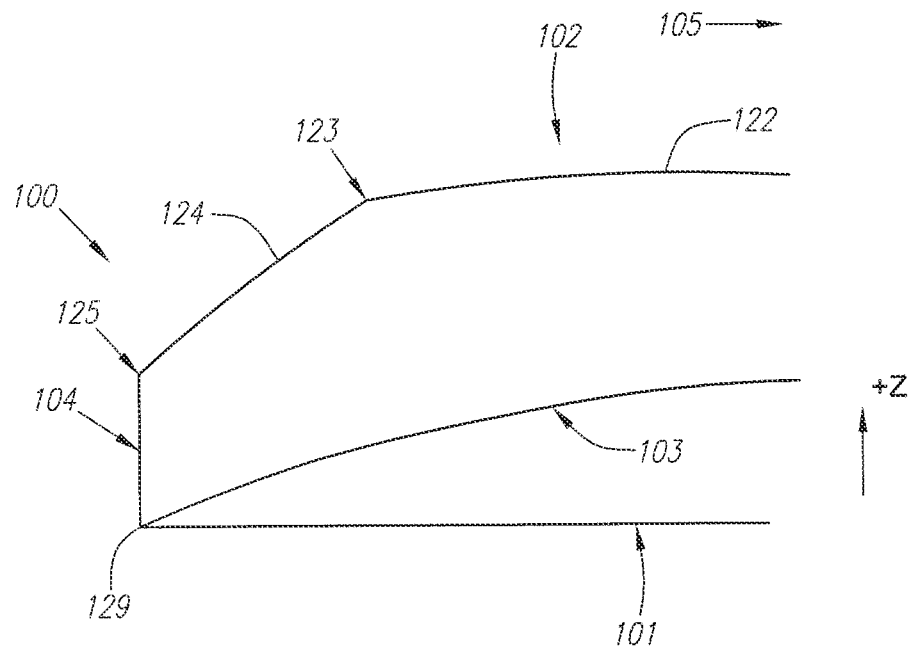

For instance, FIG. 3 is a cross-sectional view depicting an anterior portion of human eye 200 including lens 202, aqueous humor 203, ciliary body 204, iris 205 and cornea 206 with an example embodiment of lens 100 implanted therein. Here, lens 100 is shown implanted as a corneal inlay although, it should be noted that lens 100 can also be implanted as a corneal onlay in a position closer to the anterior surface of cornea 206. The gradual transition in the edge region of lens 100 facilitates the acceptance of lens 100 by the surrounding corneal tissue 207, more so than conventional lenses with an unbeveled sharp or steep transition between the anterior and posterior surfaces. As a result, lens 100 is less susceptible to undesirable conditions such as corneal haze and the like. In addition, during the implantation procedure, the modified edge region of lens 100 makes it easier to ascertain whether lens 100 is properly oriented or whether lens 100 is inverted.

In order to sustain the cornea 206 and prevent tissue necrosis, an adequate level of fluid and nutrient transfer should be maintained within cornea 206. Accordingly, lens body 101 is preferably composed of a material with a permeability sufficient to allow fluid and nutrient transfer between corneal tissue 207 adjacent to anterior surface 102 and posterior surface 103, in order to sustain the cornea over a desired period of time. For instance, in one example embodiment lens body 101 is composed of a microporous hydrogel material. Microporous hydrogels are described in further detail in U.S. Pat. No. 6,875,232 entitled "Corneal Implant and Method of Manufacture," which is fully incorporated by reference herein.

TABLE 1 depicts example values for one embodiment of a 5.0 millimeter (mm) diameter lens 100 having a given diopter. These example values are for purposes of illustration only and in no way limit the implantable lens 100 to only these or similar values.

TABLE 1

| Diopter | +2.25 |
|---|---|
| Lens diameter 112 (mm) | 5.00 |
| Corrective diameter 114 (mm) | 4.90 |
| Posterior radius 107 (mm) | 7.50 |
| Center thickness 140 (mm) | 0.030 |
| Bevel radius 124 (mm) | 5.500 |
| Edge radius 126 (mm) | 0.025 |
| Edge thickness 130 (mm) | 0.010 |
| Edge slope angle 132 (degrees) | 50 |

The values of edge thickness 130, edge radius 126, edge slope angle 132 and bevel radius 124 are interdependent and based on the desired corrective values, the overall lens diameter 112, the diameter of corrective portion 122, and the shape of anterior surface 102 and posterior surface 103. Preferably, a lens diameter 112 in the range of about 1-10 mm with a corrective portion diameter 114 of about 0.5 mm or greater will have an edge thickness less than or equal to about 0.015 mm, an edge radius 126 in the range of about 0.001-1 mm, an edge slope angle 132 between 0 and 90 degrees and a bevel radius 124 in the range of about 1-10 mm. These ranges are for illustrative purposes only and in no way limit the embodiments described herein.

It should be noted that the modified edge described herein can be used with any type, shape or configuration of implantable lens. For instance, lens 100 can be either a corneal inlay or onlay. Lens 100 can be configured to treat any visual impairment including, but not limited to, myopia, hyperopia, astigmatism, and presbyopia. Lens 100 can also be configured to treat any combination of visual impairments including, but not limited to, presbyopia with myopia or hyperopia and presbyopia with astigmatism. The overall outer profile 119 of lens 100 can be any shape, including, but not limited to, circular, elliptical, irregular, multi-sided, and shapes having an inner aperture. Outer edge surface 104 can configured with outcroppings such as fixation elements and the like. Also, lens body 101 can be fabricated from one or more different materials having any desired refractive index. Furthermore, as will be described in greater detail below, corrective portion 122 of anterior surface 102 can be substantially spherical with or without multiple focal zones, substantially aspherical with or without multiple aspherical surfaces, or any combination and the like. As used herein, the term substantially is intended to broaden the modified term. For instance, a substantially spherical surface does not have to be perfectly spherical, but can include non-spherical variations or errors and the like to a degree sufficient for implementation.

FIGS. 4-9 are cross-sectional views depicting additional example embodiments of lens 100 taken along line 1-1 in region 111 of FIG. 1B. In the embodiment depicted in FIG. 4, corrective portion 122 of anterior surface 102 is substantially aspherical. The rate of curvature of aspherical surfaces typically decreases or increases as the surface progresses outwards towards outer edge surface 104. In this embodiment, the rate of curvature of aspheric surface 122 decreases such that the surface is flatter near outer edge surface 104 than near apex 105 (not shown). Anterior surface 102 and posterior surface 103 diverge as the surfaces 102-103 progress radially outwards from apex 105 (not shown) towards interface 123. From interface 123 to interface 125, bevel radius 124 preferably converges towards posterior surface 103. Likewise, from interface 125 to interface 127, edge radius 126 also preferably converges towards posterior surface 103.

Beveled portion 124 of anterior surface 102 can be flat or curved or any other desired shape. For instance, in FIGS. 2C-E, beveled portion 124 is spherically curved, however, it should be noted that any type of curve can be used. In the embodiment depicted in FIG. 5, beveled portion 124 is flat. Likewise, first and second edge surface portions 126 and 128 can be flat or curved or any other desired shape. For instance, in FIGS. 2C-E, edge radius 126 is substantially spherically curved and second edge surface portion 128 is curved at a variable rate. In the embodiment depicted in FIG. 6, first edge surface portion 126 is flat, while in the embodiment of FIG. 7 second edge surface portion 128 is flat. Any combination of flat and curved surfaces can be implemented. For instance, in FIG. 8, beveled portion 124, and first and second edge surface portions 126 and 128 are all flat. Also, edge surface 104 can be implemented in any desired manner. For instance, in FIG. 9, edge surface 104 is flat and oriented in only the Z direction.

Figure 10A:
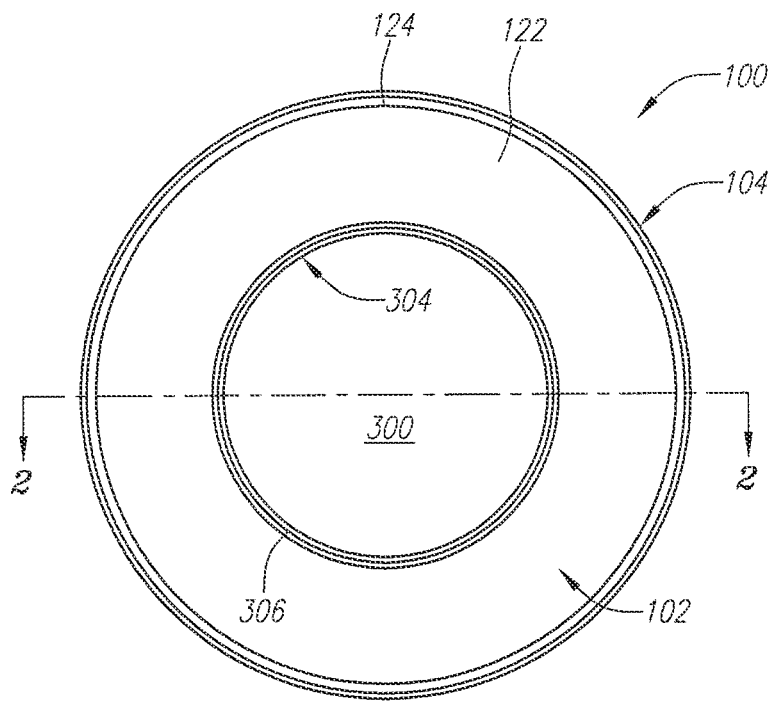
FIG. 10A is a top-down view depicting another example embodiment of the implantable lens.
Figure 10B:
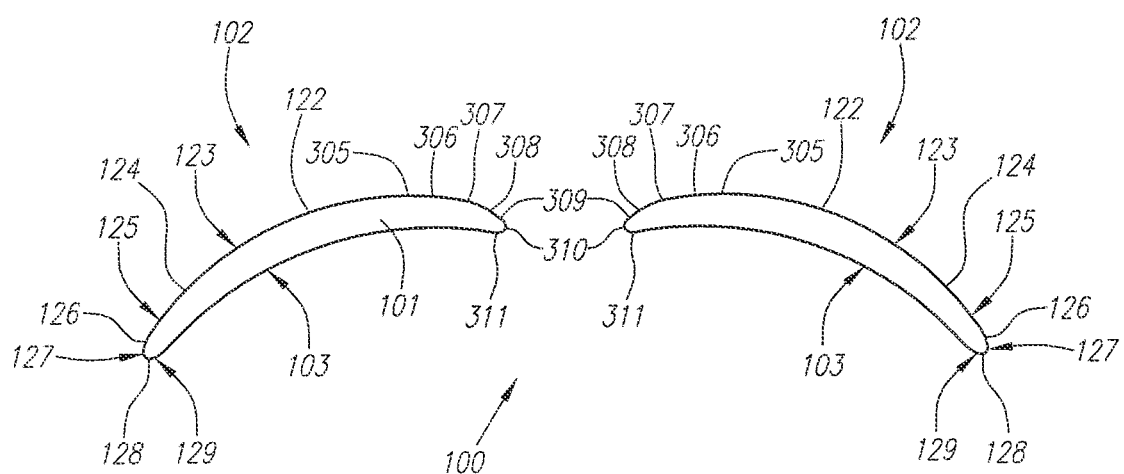
FIG. 10B is a cross-sectional view taken along line 2-2 of FIG. 10A depicting another example embodiment of the implantable lens.

FIG. 10A is a top-down view depicting another example embodiment of lens 100 having a ring-like shape. Here, lens 100 includes inner aperture 302 and inner edge surface 304. FIG. 10B is a cross-sectional view of the embodiment of lens 100 depicted in FIG. 10A taken along line 2-2. Here, it can be seen that anterior surface 102 also includes inner beveled portion 306 located between corrective portion 122 and inner edge surface 304. Like outer edge surface 104, inner edge surface 304 includes first portion 308 and second portion 310, which, in this embodiment, are both curved. Beveled portion 306 abuts corrective portion 122 at interface 305 and first portion 308 abuts beveled portion 306 at interface 307. Second portion 310 abuts first portion 308 at interface 309 and abuts posterior surface 103 at interface 311. It should be noted that edge surface 304 and beveled portion 306, like edge surface 104 and beveled portion 124 described above, can be shaped or configured in any manner desired. Lenses 100 of the type depicted in FIGS. 10A-B are described in more detail in U.S. application Ser. No. 11/032,913, entitled "Myopic Corneal Ring with Central Accommodating Portion" and filed Jan. 11, 2005, which is fully incorporated by reference herein.

Figure 11A:
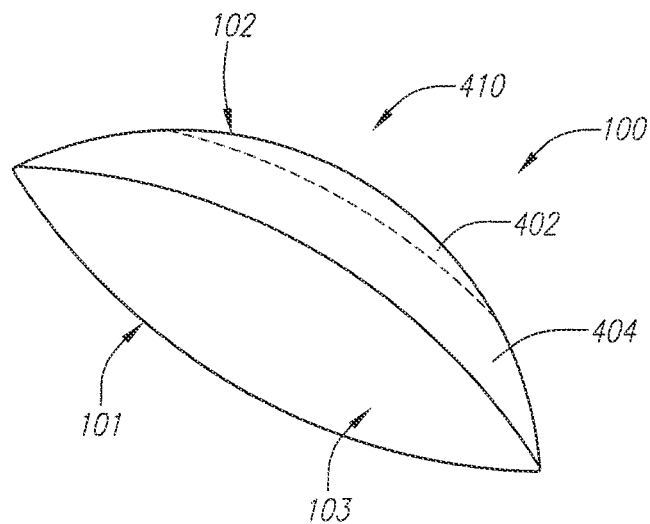
FIG. 11A is a perspective view depicting another example embodiment of the implantable lens.

As mentioned above, lens 100 with the modified edge region as described herein can also be implemented as a multifocal lens. FIG. 11A is a perspective view depicting an example embodiment of implantable lens 100 configured to provide multifocal correction. Here, lens 100 includes two corrective regions 402 and 404 each having a different refractive index. The different refractive indices in each region allow for correction of visual impairments over different distance ranges. For instance, the refractive indices of regions 402 and 404 can be predetermined such that region 402 provides refractive correction over relatively near distances while region 404 provides correction over relatively far distances or vice-versa. Any combination and number of two or more corrective regions can be used. Likewise, any refractive index can be used including refractive indices that are substantially similar to cornea 206 (about 1.36-1.39) and refractive indices that are greater than or less than that of cornea 206.

Figure 11B:
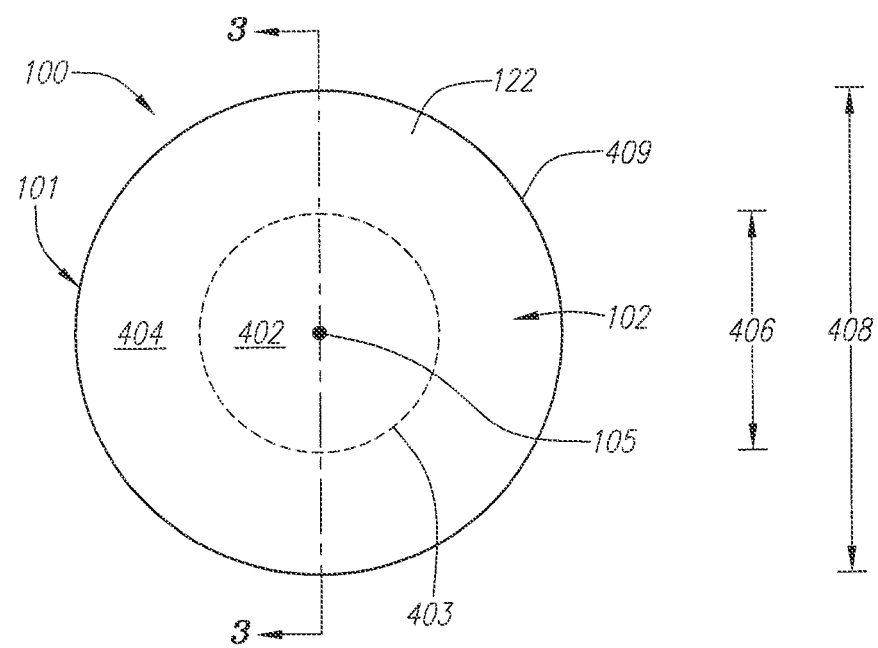
FIG. 11B is a top-down view depicting another example embodiment of the implantable lens.

FIG. 11B is a top down view depicting this embodiment of lens 100 taken along direction 410. In this embodiment, lens 100 has apex 105, a generally circular outer edge profile 409 and regions 402 and 404 have diameters 406 and 408, respectively. The transition between regions 402 and 404 is referenced as interface 403. Here, regions 402 and 403 are arranged as generally concentric circular regions. It should be noted that regions 402 and 403 can be arranged in any desired manner such as eccentric, hemispherical, irregular and the like. Also, any number of two or more regions can be implemented with any number or none of those regions being integrally coupled together.

Figure 11C:
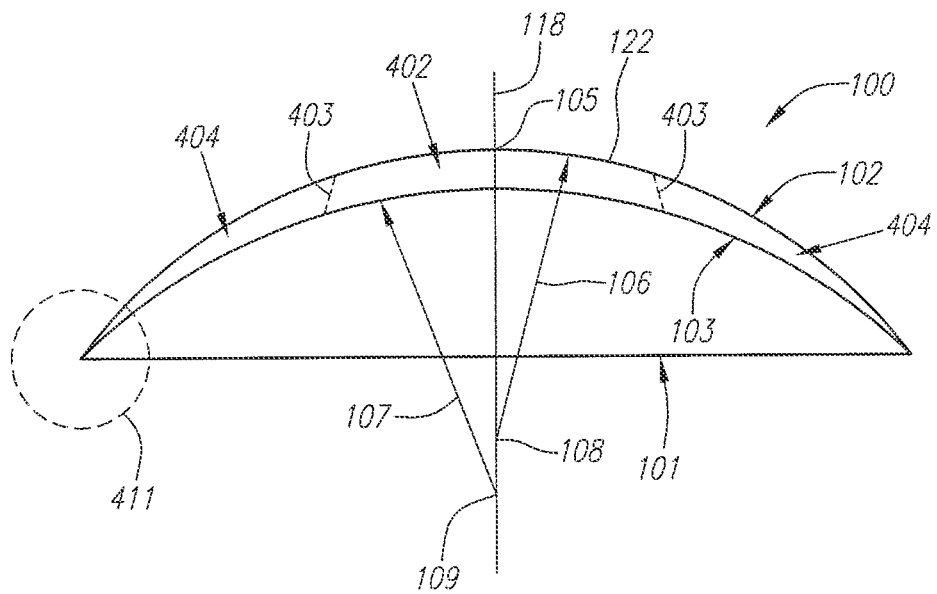
FIGS. 11C and 11D are cross-sectional views taken along line 3-3 of FIG. 11B depicting additional example embodiments of the implantable lens.
Figure 11D:
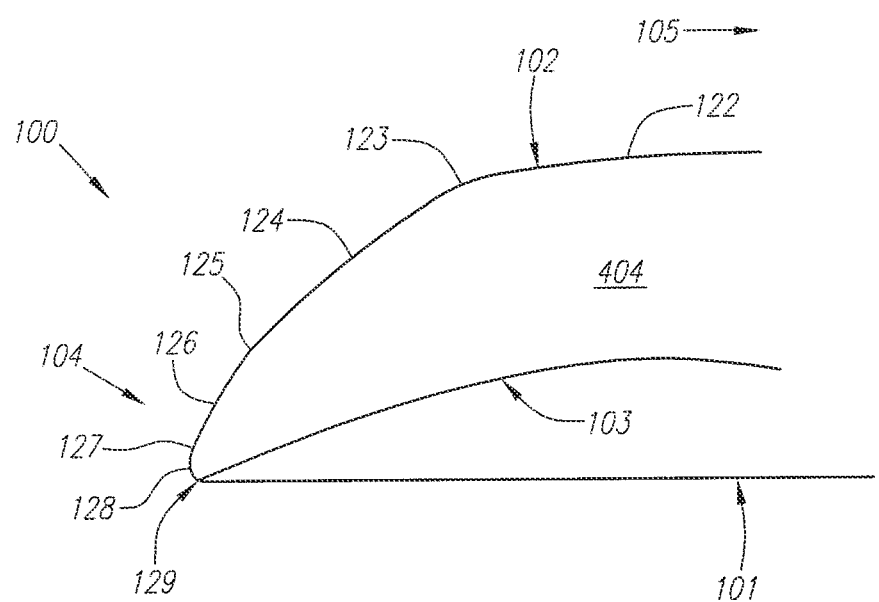

FIG. 11C is a cross-sectional view depicting the embodiment of FIG. 11B taken over line 3-3. Here, corrective portion 122 of anterior surface 102 is substantially spherical having one radius of curvature 106 and posterior surface 103 is also substantially spherical having one radius of curvature 107. Adjustment of these radii 106-107 along with the selection of the appropriate refractive index for regions 402-404 can provide the proper diopter values for each zone to treat a given individual. FIG. 11D is an enlarged cross-sectional view of this embodiment lens 100, showing region 411 of FIG. 11C in greater detail. In this embodiment, similar to the embodiment depicted in FIG. 2D, lens 100 includes bevel radius 124, edge radius 126 and curved second edge surface portion 128.

Figure 12A:
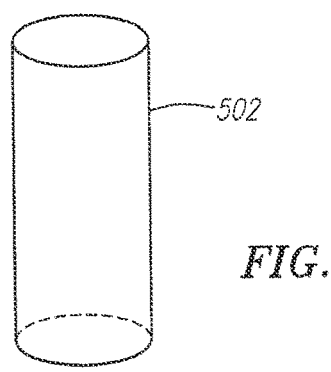
FIGS. 12A, 12B, 12C and 12D are block diagrams depicting an example method of manufacturing the implantable lens.
Figure 12B:
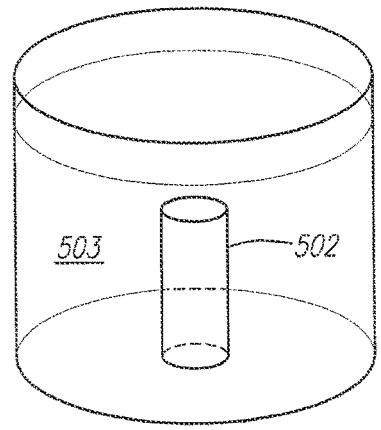
Figure 12C:
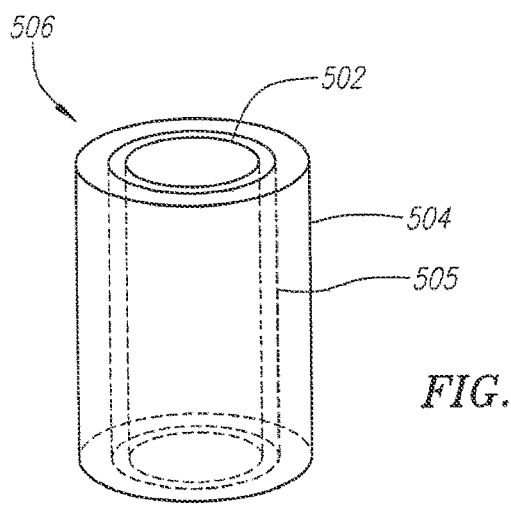
Figure 12D:
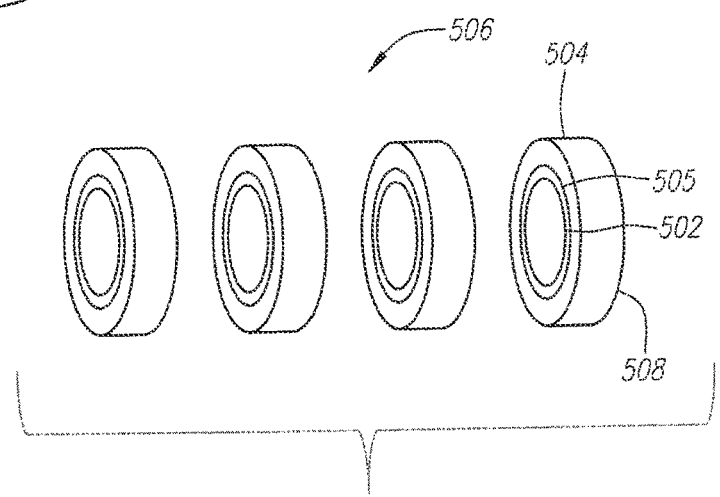

To provide different refractive indices, in one example embodiment regions 402 and 404 are fabricated from different materials integrally coupled together at interface 403. For instance, each region 402 and 404 can be fabricated from different microporous hydrogel materials. In one example embodiment, lens 100 is fabricated by first forming a solid polymeric cylindrical core 502, such as that depicted in FIG. 12A, which corresponds to region 402 and has approximately the same diameter as diameter 406 of region 402. This core can then be surrounded by a monomeric solution 503 in a manner similar to that depicted in FIG. 12B. Polymeric core 502 is preferably at least slightly soluble in monomeric solution 503. Monomeric solution 503 can then be polymerized to form outer polymeric cylindrical region 504 surrounding inner core 502 as depicted in FIG. 12C. Outer region 504 preferably corresponds to region 404 and has approximately the same diameter or a slightly larger diameter than diameter 408 of region 404. Inner core 502 and outer region 504 together form lens core 506, from which one or more lens can be fabricated, such as, for instance, by separating core 506 into disc-shaped buttons 508 as depicted in FIG. 12D. Each individual button can be machined or cut into the desired shape and further processed (e.g., softened, hydrated, etc.) to form an individual lens body 101.

As mentioned above, polymeric core 502 is preferably at least slightly soluble in monomeric solution 503. This is so that solution 503 can dissolve the outer surface of core 502 and become interspersed and mixed with the dissolved portion of core 502. Once solution 503 is polymerized and solidified, an interface region 505 between cores 502 and 504 can be formed where the different polymers in cores 502 and 504 together form an interpenetrating network. This interface region corresponds to interface region 430 in FIG. 13 below and integrally couples regions 402 and 404 together.

Figure 13:
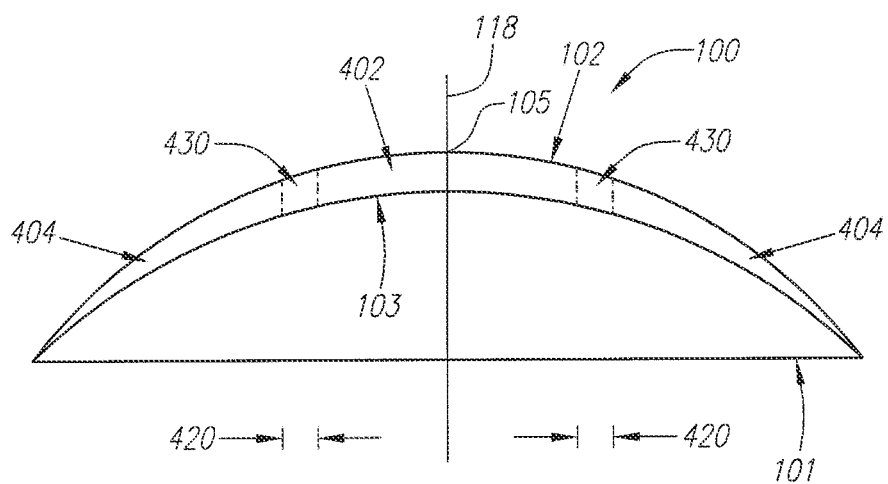
FIG. 13 is a cross-sectional view depicting another example embodiment of the implantable lens.

FIG. 13 is a cross-sectional view of an example embodiment of lens 100 having interface region 430. By integrally coupling regions 402 and 404 together, interface region significantly reduces the risk that regions 402 and 404 will separate, such as can be the case when an adhesive is used to join regions 402 and 404. Furthermore, interface region 430 can have a refractive index or range of refractive indices between the refractive indices of regions 402 and 404. As a result, interface region 430 can act as an optical transition between regions 402 and 404 and add a third multifocal region to lens 100. This can eliminate an immediate or sharp transition between the refractive indices of regions 402 and 404 that could result in visual artifacts such as halo or glare.

The width 420 of interface region 430 can be varied as desired. For instance, to generate a wider interface region 430, monomeric solution 504 can be left in contact with inner core 502 for a longer period of time before polymerization, or, the solubility of inner polymeric core 502 in monomeric solution 504 can be increased. Generally, the wider interface region 430 becomes, the more noticeable region 430 to the subject as a multifocal region.

It should be noted that lens 100 can be fabricated in any manner and is not limited to the example described with respect to FIGS. 12A-12D. Other polymerization methods known in the art including, but not limited to, dip coating, spinning, casting, and the polymerization of pre-polymers, can be used in the formation of regions 402 and 404.

In another example embodiment, each region 402 and 404 is configured with varying levels of permeability. For instance, region 402 can have a level of permeability to fluid and nutrients that is sufficient to substantially sustain cornea 206, while region 404 can have a permeability to either fluid or fluid and nutrients that is relatively less than region 402, including being entirely impermeable to fluid and nutrients. This allows for the use of more types of materials having a wider range of refractive indices and/or structural characteristics.

In order to allow enough fluid/nutrient transfer to sustain cornea 206, the size of any impermeable region is preferably minimized. For instance, any circular central region, similar to the embodiment of region 402 described with respect to FIG. 11B, that is impermeable to fluid and nutrients is preferably less than about 3 mm in diameter (diameter 406) or about 7.1 square mm. However, it should be noted that lens 100 is not limited to any one total impermeable surface area, the size and surface area of any impermeable region being dependent on the shape of the region and the relative level of permeability of any accompanying regions. For instance, an example embodiment of lens 100 having many concentric regions arranged in a bullseye fashion where the regions alternate between permeable and impermeable could allow for a total surface area of impermeable regions that is greater than 7.1 square mm.

Figure 14A:
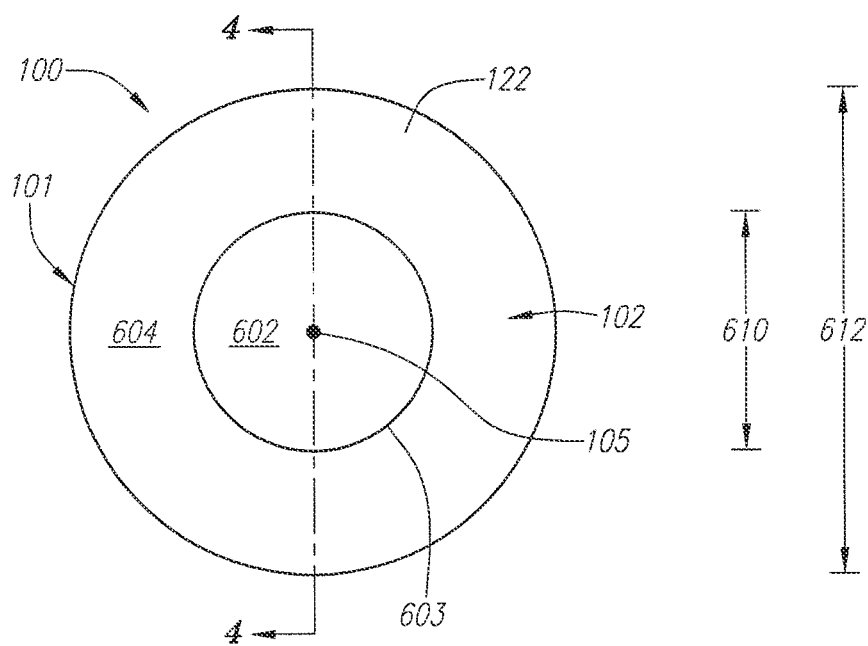
FIG. 14A is a top-down view depicting another example embodiment of the implantable lens.
Figure 14B:
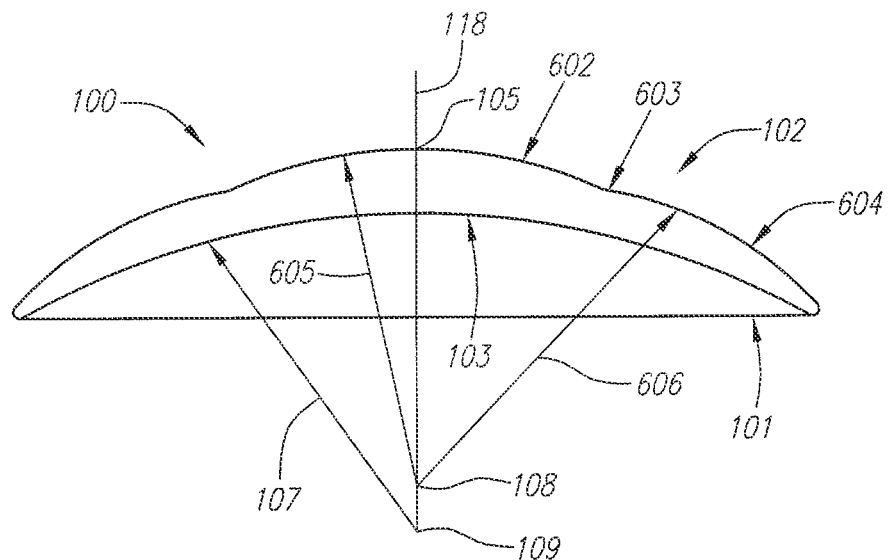
FIGS. 14B and 14C are cross-sectional views taken along line 4-4 of FIG. 14A depicting additional example embodiments of the implantable lens.

FIG. 14A is a top-down view depicting another example embodiment of multifocal lens 100 where corrective portion 122 of anterior surface 102 includes surfaces 602 and 604 having different rates of curvature. Surfaces 602 and 604 have diameters 610 and 612, respectively. FIG. 14B is a cross-sectional view of another example embodiment of lens 100 taken along line 4-4 of FIG. 14A. Here, surfaces 602 and 604 are each substantially spherical but have different radii of curvature 605 and 606, respectively. The abutment between surface 602 and 604 is referenced as interface 603. Each surface 602 and 604 can be configured with a different diopter value to correct for separate distances ranges (e.g., near-far, far-near, etc.). TABLE 2 depicts example values for three embodiments of a 5.0 millimeter (mm) diameter lens 100 having multiple spherical surfaces 602 and 604 similar to that depicted in FIG. 14B. Each of the three embodiments provides for a different degree of correction for relatively far distances (sphere) and relatively near distances (add). These corrective values are shown in the format "sphere diopter/add diopter." All of these example values are for purposes of illustration only and in no way limit the implantable lens 100 to only these or similar values.

TABLE 2

| Parameter | 0.00/1.75 | 0.00/2.00 | 0.00/2.25 |
|---|---|---|---|
| Lens diameter 112 (mm) | 5.00 | 5.00 | 5.00 |
| Posterior radius 107 (mm) | 7.50 | 7.50 | 7.50 |
| Center thickness 140 (mm) | 0.020 | 0.021 | 0.022 |
| Bevel radius 124 (mm) | 4.770 | 4.770 | 4.770 |
| Edge radius 126 (mm) | 0.025 | 0.050 | 0.050 |
| Edge thickness 130 (mm) | 0.010 | 0.010 | 0.010 |
| Edge slope angle 132 (degrees) | 45 | 45 | 45 |
| Spherical Surface 602 | | | |
| Diameter 610 (mm) | 2.00 | 2.00 | 2.00 |
| Radius 605 (mm) | 7.252 | 7.217 | 7.182 |
| Spherical Surface 604 | | | |
| Diameter 612 (mm) | 4.90 | 4.90 | 4.90 |
| Radius 606 (mm) | 7.505 | 7.505 | 7.505 |

Figure 14C:
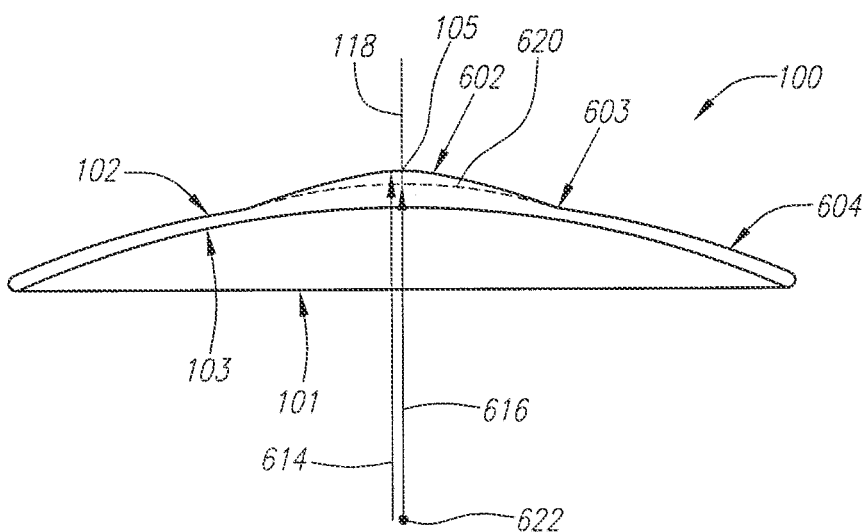

FIG. 14C is a cross-sectional view of another example embodiment of lens 100 taken along line 4-4 of FIG. 14A. Here, surfaces 602 and 604 are each substantially aspherical. Surfaces 602 and 604 each have a radius 614 and 616, respectively, measured along central axis 118. Radius 616 is measured along central axis 118 from vertex 622 to an imaginary position of surface 604 corresponding to the point where surface 604 would intersect central axis 118 if surface 604 were to extend all the way to central axis 118 as indicated by dashed line 620.

Because aspherical surfaces are inherently multifocal, the inclusion of multiple aspherical surfaces provides an added dimension of multifocality to lens 100. For instance, surface 602 can have any asphericity (Q) and can provide a range of diopter values varying at any rate from apex 105 to interface 603 and can be configured to provide for correction over relatively near distances, while surface 604 can have a range of diopter values varying at any rate from interface 603 to interface 123 and can be configured to provide correction over relatively far distances. One of skill in the art will readily recognize that each surface 602 and 604 can have any range of diopter values and provide for correction over any distance.

TABLE 3 depicts example values for one embodiment of a 5.0 millimeter (mm) diameter lens 100 having multiple aspherical surfaces 602 and 604 similar to that depicted in FIG. 14C. Each of the three embodiments provides for a different degree of correction for relatively far distances and relatively near distances. All of these example values are for purposes of illustration only and in no way limit the implantable lens 100 to only these or similar values.

TABLE 3

| Parameter | 0.00/1.75 D | 0.00/2.00 D | 0.00/2.25 D |
|---|---|---|---|
| Lens diameter 112 (mm) | 5.00 | 5.00 | 5.00 |
| Posterior radius 107 (mm) | 7.50 | 7.50 | 7.50 |
| Center thickness 140 (mm) | 0.020 | 0.021 | 0.022 |
| Bevel radius 124 (mm) | 4.770 | 4.770 | 4.770 |
| Edge radius 126 (mm) | 0.025 | 0.025 | 0.025 |
| Edge thickness 130 (mm) | 0.010 | 0.010 | 0.010 |
| Edge slope angle 132 (degrees) | 45 | 45 | 45 |
| Aspherical Surface 602 | | | |
| Diameter 610 (mm) | 2.00 | 2.00 | 2.00 |
| Radius 614 (mm) | 7.217 | 7.182 | 7.148 |
| Asphericity (Q) | −1.015 | −1.001 | −0.987 |
| Aspherical Surface 604 | | | |
| Diameter 612 (mm) | 4.90 | 4.90 | 4.90 |
| Radius 616 (mm) | 7.452 | 7.452 | 7.452 |
| Asphericity (Q) | −0.225 | −0.225 | −0.225 |

Although not depicted in FIGS. 14A-C, lens 100 can have one or more transition surfaces at interface 603 that provide for a smoother transition between surfaces 602 and 604, as sharp transitions can stimulate adverse tissue reactions. Edge surface 104 and beveled portion 124 are also not depicted in FIGS. 14A-C, but it can be included as desired. Also, it should be noted that lens 100 can have any number of multifocal surfaces or refractive regions as desired. The multifocal surfaces 602 and 604, substantially spherical or substantially aspherical, can also be arranged in any manner desired including, but not limited to, eccentric, hemispherical, irregular and the like.

Figure 15:
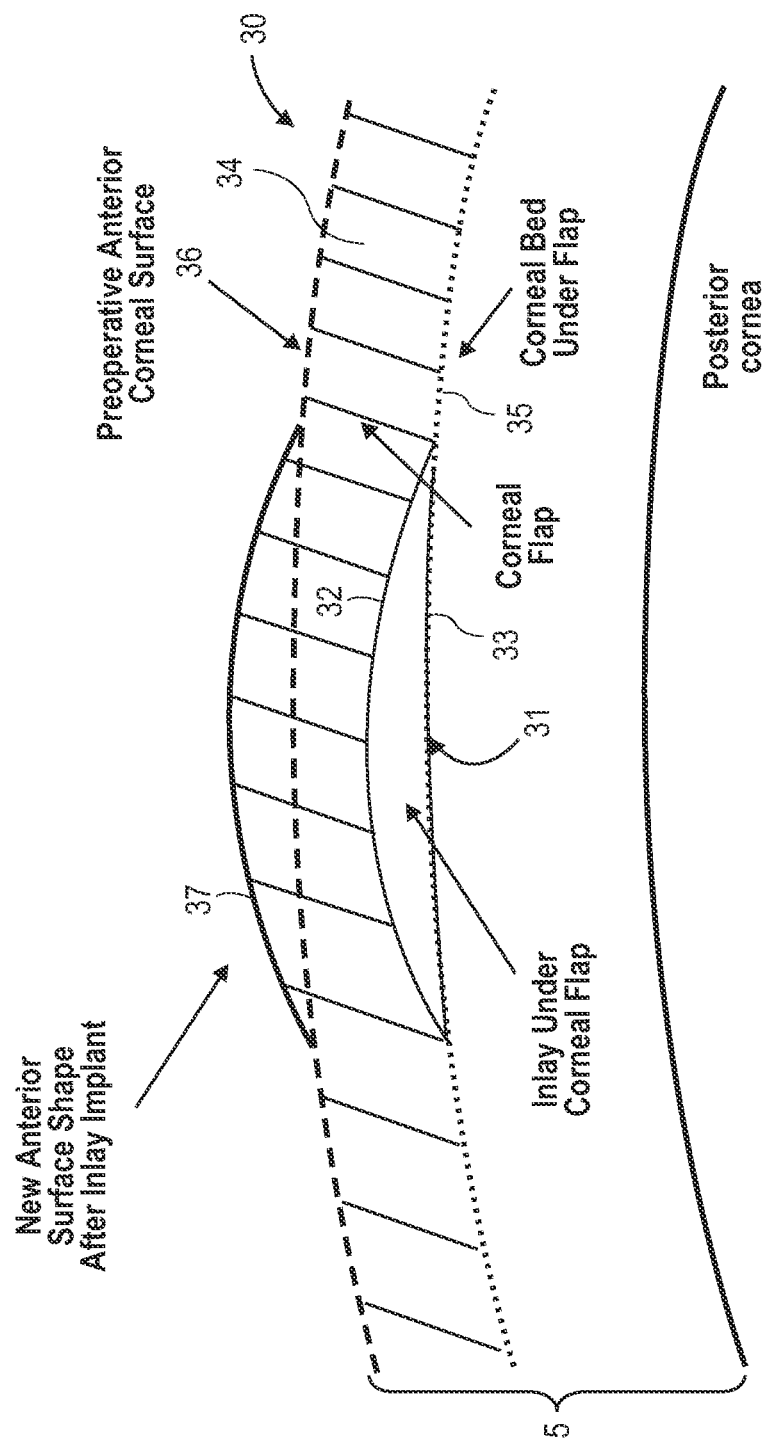
FIG. 15 is a cross-sectional view of a cornea showing an intracorneal inlay implanted in the cornea according to an embodiment of the invention.

FIG. 15 shows an example of an intracorneal inlay 31 implanted in a cornea 30. The inlay 31 may have a meniscus shape with an anterior surface 32 and a posterior surface 33. The inlay 31 is preferably implanted in the cornea at a depth of 50% or less of the cornea (approximately 250 microns or less), and is placed on the stromal bed 35 of the cornea created by a micro keratome. The inlay 31 may be implanted in the cornea 30 by cutting a flap 34 into the cornea, lifting the flap 34 to expose the cornea's interior, placing the inlay 31 on the exposed area of the cornea's interior, and repositioning the flap 34 over the inlay 31. The flap 34 may be cut using a laser, e.g., a femtosecond laser, a mechanical keratome or manually by an ophthalmic surgeon. When the flap 34 is cut into the cornea, a small section of corneal tissue is left intact to create a hinge for the flap 34 so that the flap 34 can be repositioned accurately over the inlay 33. After the flap 34 is repositioned over the inlay, the cornea heals around the flap 34 and seals the flap 34 back to the un-cut peripheral portion of the anterior corneal surface. Alternatively, a pocket or well having side walls or barrier structures may be cut into the cornea, and the inlay inserted between the side walls or barrier structures through a small opening or "port" in the cornea.

The inlay 31 changes the refractive power of the cornea by altering the shape of the anterior corneal surface. In FIG. 15, the pre-operative anterior corneal surface is represented by dashed line 36 and the post-operative anterior corneal surface induced by the underlying inlay 31 is represented by solid line 37.

The inlay may have properties similar to those of the cornea (e.g., index of refraction around 1.376, water content of 78%, etc.), and may be made of hydrogel or other clear bio-compatible material. To increase the optical power of the inlay, the inlay may be made of a material with a higher index of refraction than the cornea, e.g., >1.376. Materials that can be used for the inlay include, but are not limited to, Lidofilcon A, Poly-HEMA, poly sulfone, silicone hydrogel, and the like. The index of refraction may be in the range of 1.33 to 1.55.

This section discusses the use of small intracorneal inlays having diameters that are small in comparison with the pupil for correcting presbyopia. In the preferred embodiment, a small inlay (e.g., 1 to 2 mm in diameter) is implanted centrally in the cornea to induce an "effect" zone on the anterior corneal surface that is smaller than the optical zone of the cornea for providing near vision. Here, "effect" zone is the area of the anterior corneal surface affected by the inlay. The implanted inlay increases the curvature of the anterior corneal surface within the "effect" zone, thereby increasing the diopter power of the cornea within the "effect" zone. Distance vision is provided by the region of the cornea peripheral to the "effect" zone.

Presbyopia is characterized by a decrease in the ability of the eye to increase its power to focus on nearby objects due to a loss of elasticity in the crystalline lens with age. Typically, a person suffering from Presbyopia requires reading glasses to provide near vision.

Figure 16:
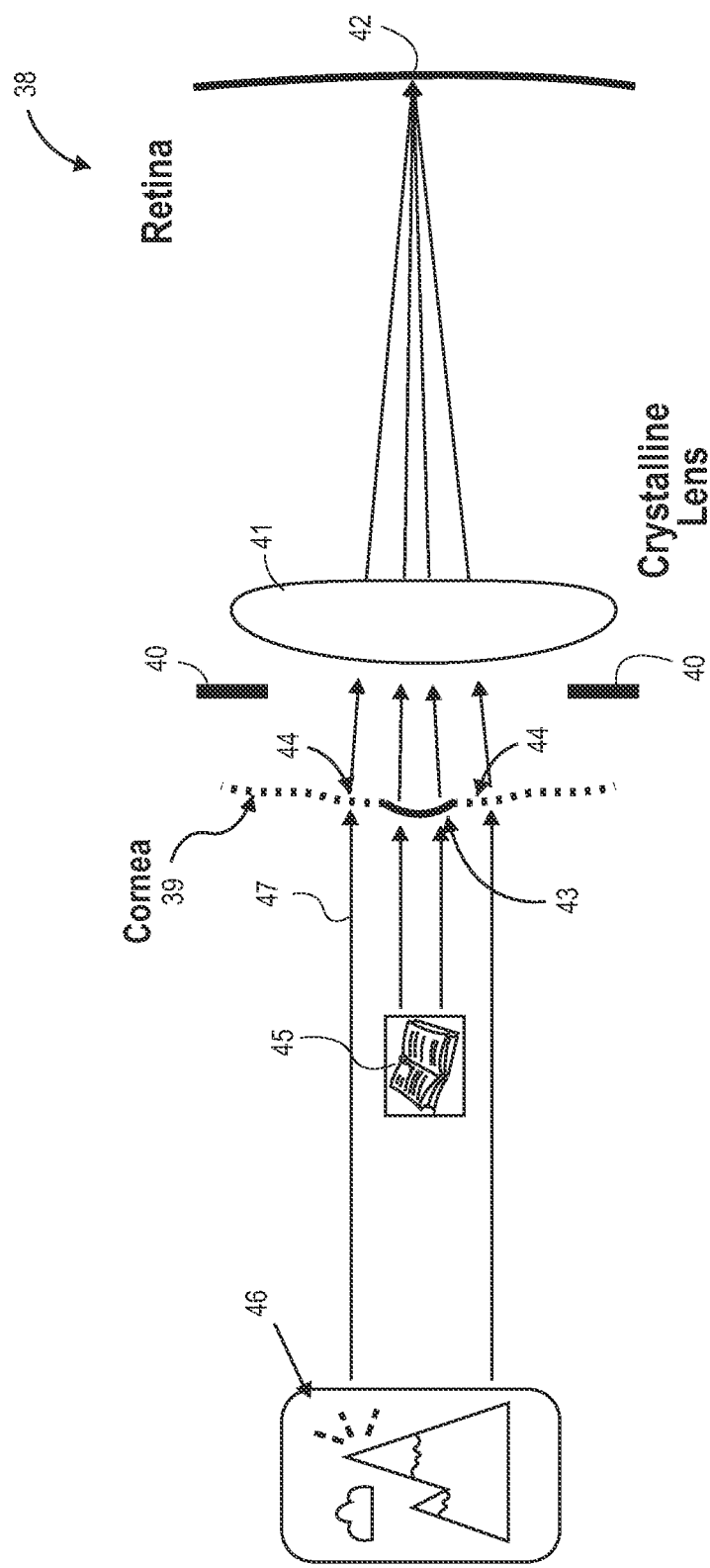
FIG. 16 is a diagram of an eye illustrating the use of a small diameter inlay to provide near vision according to an embodiment of the invention.

FIG. 16 shows an example of how a small inlay can provide near vision to a subject's eye while retaining some distance vision according to an embodiment of the invention. The eye 38 comprises the cornea 39, the pupil 40, the crystalline lens 41 and the retina 42. In this example, the small inlay (not shown) is implanted centrally in the cornea to create a small diameter "effect" zone 43. The small inlay has a smaller diameter than the pupil 40 so that the resulting "effect" zone 43 has a smaller diameter than the optical zone of the cornea. The "effect" zone 43 provides near vision by increasing the curvature of the anterior corneal surface, and therefore the diopter power within the "effect" zone 43. The region 44 of the cornea peripheral to the "effect" zone provides distance vision.

To increase the diopter power within the "effect" zone 43, the small inlay has a higher curvature than the pre-implant anterior corneal surface to increase the curvature of the anterior corneal surface within the "effect" zone 43. The inlay may further increase the diopter power within the "effect" zone 43 by having an index of refraction that is higher than the index of refraction of the cornea ($n_{cornea}$=1.376). Thus, the increase in the diopter power within the "effect" zone 43 may be due to the change in the anterior corneal surface induced by the inlay or a combination of the change in the anterior cornea surface and the index of refraction of the inlay. For early presbyopes (e.g., about 45 to 55 years of age), at least 1 diopter is typically required for near vision. For complete presbyopes (e.g., about 60 years of age or older), between 2 and 3 diopters of additional power is required.

An advantage of the small intracorneal inlay is that when concentrating on nearby objects 45, the pupil naturally becomes smaller (e.g., near point miosis) making the inlay effect even more effective. Further increases in the inlay effect can be achieved by simply increasing the illumination of a nearby object (e.g., turning up a reading light).

Because the inlay is smaller than the diameter of the pupil 40, light rays 47 from distant objects 46 by-pass the inlay and refract using the region of the cornea peripheral to the "effect" zone to create an image of the distant objects on the retina 42, as shown in FIG. 16. This is particularly true with larger pupils. At night, when distance vision is most important, the pupil naturally becomes larger, thereby reducing the inlay effect and maximizing distance vision.

A subject's natural distance vision is in focus only if the subject is emmetropic (i.e., does not require glasses for distance vision). Many subjects are ammetropic, requiring either myopic or hyperopic refractive correction. Especially for myopes, distance vision correction can be provided by myopic Laser in Situ Keratomileusis (LASIK), Laser Epithelial Keratomileusis (LASEK), Photorefractive Keratectomy (PRK) or other similar corneal refractive procedures. After the distance corrective procedure is completed, the small inlay can be implanted in the cornea to provide near vision. Since LASIK requires the creation of a flap, the inlay may be inserted concurrently with the LASIK procedure. The inlay may also be inserted into the cornea after the LASIK procedure since the flap can be re-opened. Therefore, the small inlay may be used in conjunction with other refractive procedures, such as LASIK for correcting myopia or hyperopia.

Figure 17:
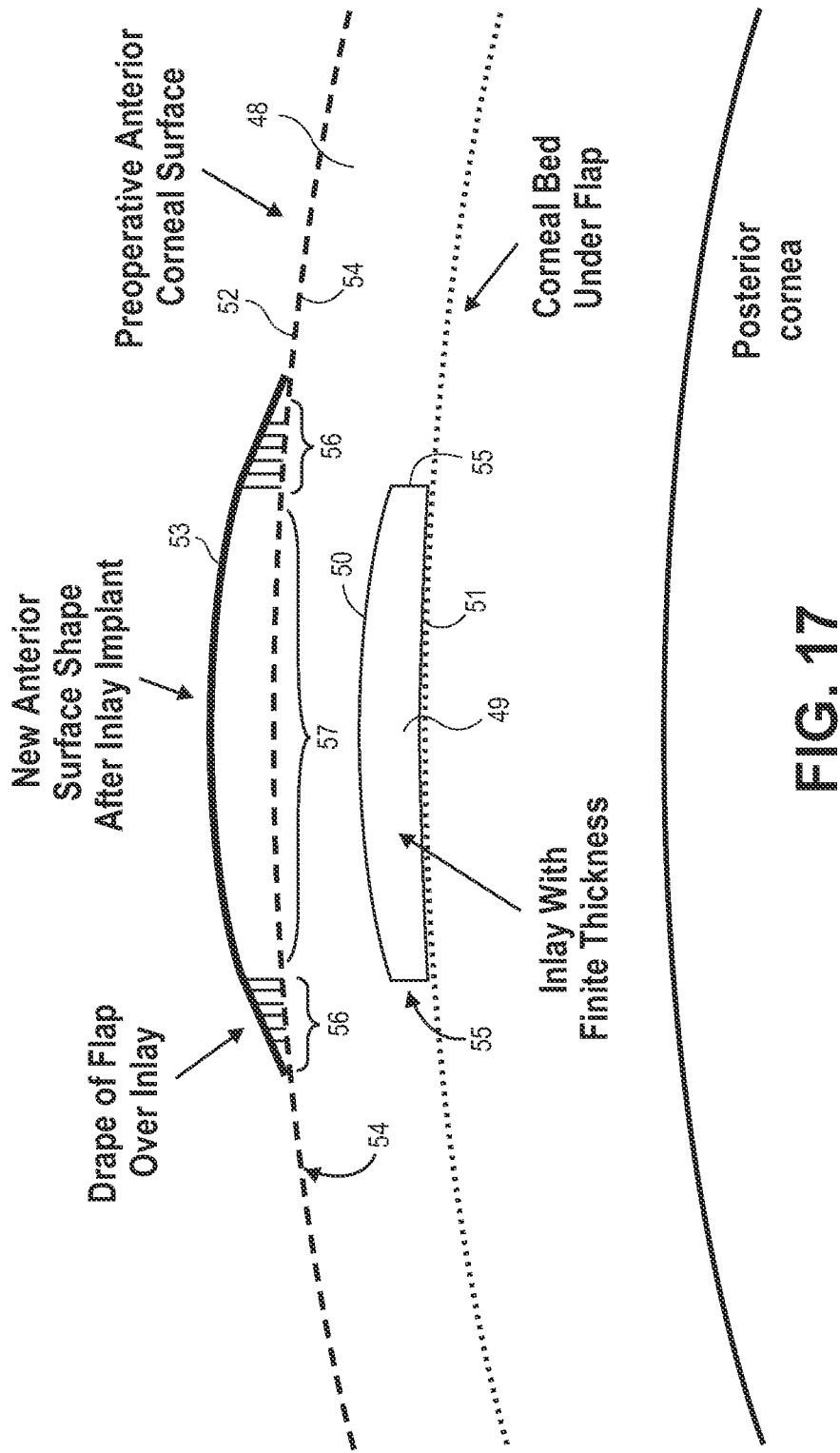
FIG. 17 is a cross-sectional view of a cornea showing an inlay implanted in the cornea and a change in the anterior corneal surface induced by the, inlay including a drape region according to an embodiment of the invention.

A method for designing a small inlay to provide near vision will now be described. FIG. 17 shows a small inlay 49 implanted in the cornea 48 and the change in the shape of the anterior corneal surface 53 induced by the inlay 49. In FIG. 17, the pre-implant anterior corneal surface is represented by dashed line 52 and the post-implant anterior corneal surface induced by the inlay 49 is represented by solid line 53. The inlay 49 does not substantially affect the shape of the anterior corneal surface in the region of the cornea peripheral to the "effect" zone so that distance vision is undisturbed in the peripheral 54. In the case where a distance corrective procedure is performed prior to implantation of the inlay, the pre-implant anterior corneal surface 52 is the anterior corneal surface after the distance corrective procedure but before implantation of the inlay.

The inlay 49 has a finite edge thickness 55. The edge thickness 55 can not be made zero due to the finite material properties of the inlay. The finite edge thickness 55 of the inlay produces a draping effect, as described further below. To minimize the draping effect, the edge thickness 55 of the inlay 49 can be made as small as possible, e.g., less than about 20 microns. In addition to a finite edge thickness 55, the inlay may have a tapered region (not shown) that tapers downward from the anterior surface 50 of the inlay to the edge 55 of the inlay. The tapered region may be 10-30 microns in length.

In FIG. 17, the portion of the anterior corneal surface directly above the inlay is altered by the physical shape of the inlay 49. Because of the finite edge thickness 55 of the inlay 49, the anterior corneal surface does not immediately return to its pre-implant shape for a diameter larger than the physical inlay 49. Eventually, the anterior corneal surface returns to the pre-implant corneal surface 52. Therefore, the draping effect produces a drape region 56 that extends the shape change of the anterior corneal surface induced by the inlay 49.

Figure 18:
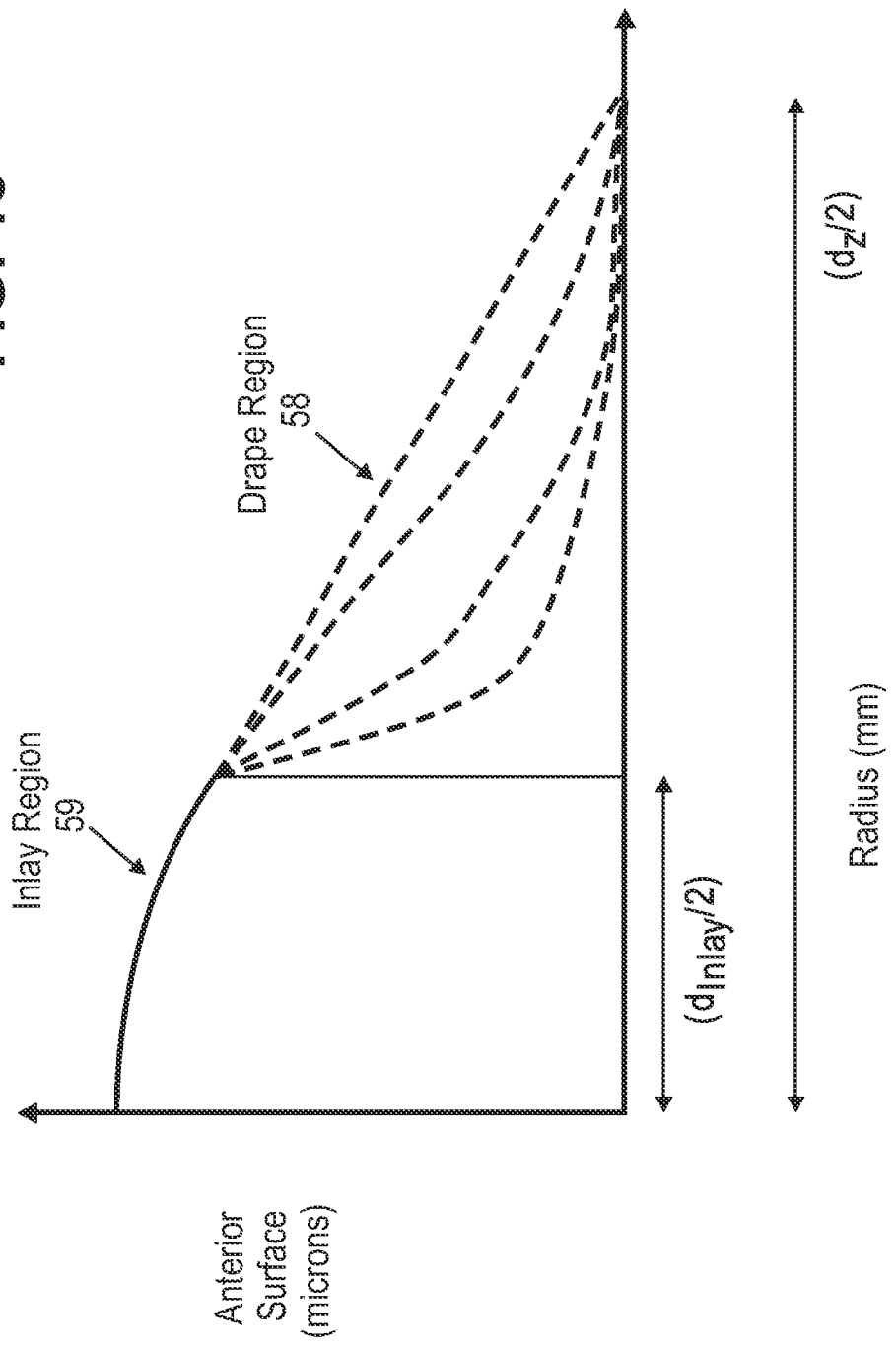
FIG. 18 illustrates various possible shapes for the drape region.

FIG. 18 illustrates a variety of possible draping shapes 58. FIG. 18 shows the radius ($d_I/2$) of an inlay region 59 and the total radius ($d_Z/2$) of the shape change due to the draping effect. The possible draping shapes 58 are shown in dashed lines, and may depend on factors such as the edge thickness, the local mechanical properties of the flap material, the diameter of the inlay (dI), the mechanical properties of the inlay material, and other geometric factors. The precise shape of the drape can be approximated by invitro or invivo clinical experiments and/or by complex mechanical modeling using techniques such as finite element analysis.

It is useful to define the optical zone diameter ($d_Z$) corresponding to the size of the anterior corneal surface affected by the inlay 49, as shown in FIG. 17. For purposes of the design method, it is sufficient to assume that the relationship between the optical zone and the inlay diameter, given the other variables, can be determined by the methods outlined above.

A method for designing a small inlay to provide near vision according to an embodiment will now be given.

(1) The first step is to determine the maximum optical zone ($d_Z$) that is an acceptable tradeoff between the near vision improvement and the loss of distance vision. Considerations include the pupil size of the specific subject or a group of characteristic subjects (e.g., subjects within a particular age range) while reading nearby objects and the pupil size for distance viewing, especially at night. In an exemplary application, the inlay is placed in one eye to provide near vision and distance correction by other means is performed on the fellow eye. In this example, both eyes contribute to distance vision, with the non-inlay eye providing the sharpest distance vision. The eye with the inlay provides near vision.

(2) Given the empirically derived or theoretically derived relationship between the optical zone ($d_Z$) and the inlay diameter (dl), approximate the inlay diameter that achieves the optical zone.

(3) Design the inlay using the method outlined in detail below. This method is similar to the design methods described in U.S. application Ser. No. 11/293,644, titled "Design of Intracorneal Inlays," filed on Dec. 1, 2005, the entirety of which is incorporated herein by reference.

(4) Finally, use optical ray-trace methods to assess the image quality of distance and near images with the inlay using the entire corneal surface (i.e., the corneal surface within the inlay diameter (dl), between the inlay diameter and the optical zone ($d_Z$), and the peripheral to the optical zone). Make small adjustments to the inlay design to optimize the distance and near image quality based on the inlay design method outlined below and the predicted drape shape given by the methods described above.

The design method of step three will now be given.

FIGS. 17 and 18 show two regions affected by the inlay design: a "central region" 57 defined by the inlay diameter (dl), and a "drape region" 56 falling between the inlay diameter and the optical zone ($d_Z$). The design method described below is used to design inlays to produce desired shapes of the anterior corneal surface in the central region to correct presbyopia. This design method assumes that the inlay material has the same index of refraction as the cornea.

A first step in the design of an inlay in the central region is determining a thickness profile that the inlay must induce on the anterior corneal surface to produce a desired anterior corneal curvature. The desired ADD power needed to provide near focus dictates the desired anterior corneal curvature in the central region (FIG. 18).

A first step in determining the thickness profile of the inlay is to determine an anterior radius of curvature, $r'_a$, that provides the desired refractive change, $\Delta Rx = Rxdist - ADD$, where ADD is the desired ADD power prescribed for near vision and Rxdist is the distance refraction prior to inlay implant. Rxdist is approximately zero diopters for emmetropic individuals, or is equal to the achieved or targeted post-operative distance refraction after a surgical procedure to correct the distance ammetropia. The equivalent change in the cornea's refractive power, $\Delta K_{equiv}$, at the anterior surface is given by:

$$\Delta K_{equiv} = \frac{1}{1/Rxdist - V} - \frac{1}{1/ADD - V} \quad \text{Equation 1}$$

where V is a spectacle vertex distance, e.g., 0.012 meters, from a spectacle to the cornea's anterior surface. The spectacle vertex distance, V, takes into account that measurements of the cornea's refractive power are typically taken with a spectacle located a distance from the cornea's anterior surface, and translates these power measurements to the equivalent power at cornea's anterior surface.

The pre-implant refractive power at the anterior corneal surface may be approximated by Kavg−Kpost, where Kavg is the average corneal refractive power within approximately the optical zone created by the inlay and Kpost is a posterior corneal refractive power. The desired radius of curvature, $r'_a$, of the anterior surface may be given by:

$$r'_a = \frac{(1.376 - 1)}{(Kavg - Kpost + \Delta K_{equiv})} \quad \text{Equation 2}$$

For purposes of design and analysis, Kpost may be approximated as −6 diopters. The pre-implant radius of curvature, $r_{preimplant}$, may be approximated by:

$$r_{preimplant} = (1.376 - 1)/(Kavg - Kpost) \quad \text{Equation 3}$$

The two radii of curvature need not originate from the same origin.

Figure 19:
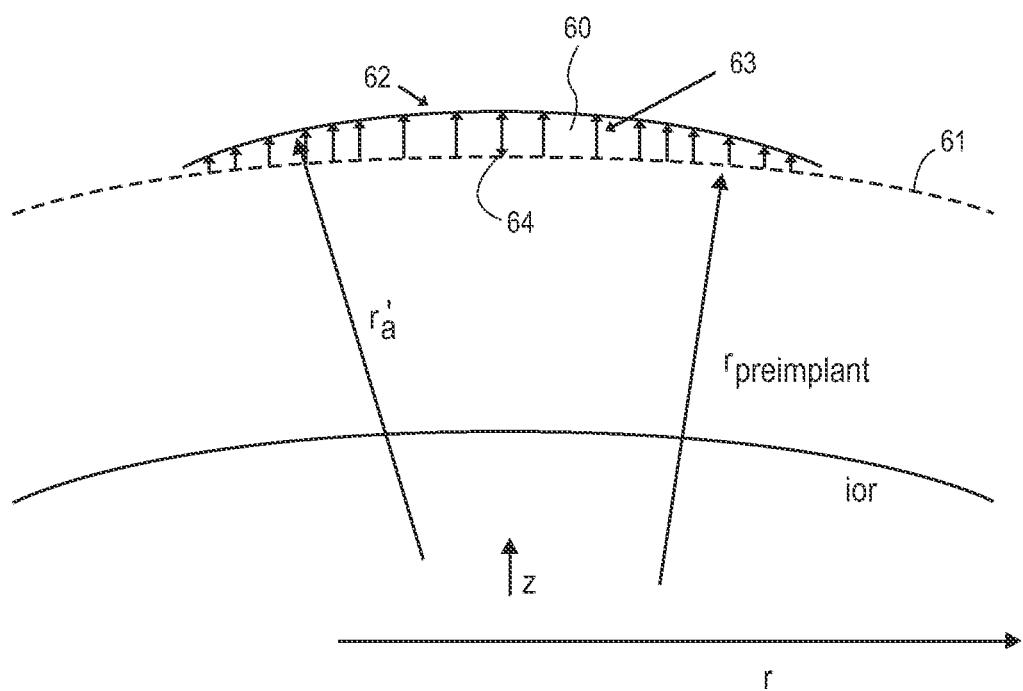
FIG. 19 is a cross-sectional view of a cornea showing a thickness profile for providing a desired refractive correction according to an embodiment of the invention.

FIG. 19 shows a cross-sectional view of a thickness profile 60 specified by a difference between the desired anterior corneal surface 62 and the pre-implant anterior corneal surface 61. In FIG. 19, arrows 63 pointing from the pre-implant anterior surface 61 to the desired anterior surface 62 represent the axial thickness, L(r), of the thickness profile 60 at different positions along an r axis that is substantially perpendicular to an optical z axis. The double arrow 64 represents a center thickness, $L_c$, of the thickness profile. In this embodiment, the thickness profile 60 is rotationally symmetric about the z axis. Thus, the entire thickness profile may be defined by rotating the cross-sectional view shown in FIG. 19 about the z axis.

The thickness L(r) of the thickness profile may be given by:

$$L(r) = +Z_{preimplant}(r; r_{preimplant}) - Z_{anew}(r; r'_a) \text{ and}$$

$$L_c = z_{anew}(d_I/2) - Z_{preimplant}(d_I/2) \quad \text{Equation 4}$$

where $L_c$ is the center thickness of the thickness profile, $Z_{implant}(r)$ is the pre-operative anterior corneal surface as a function of r, $Z_{anew}(r)$ is the desired anterior corneal surface as a function of r, and $d_I$ is the diameter of the inlay. In the example above, the anterior surfaces $Z_{anew}$ and $Z_{preimplant}$ were assumed to be spherical. This need not be the case. The anterior surfaces may also be aspheric. More generally, the desired anterior surface $Z_{anew}$ may be a function of desired ADD and also more complex design parameters, e.g., an aspheric surface for higher-order aberration correction. Also, the pre-implant anterior surface $Z_{preimplant}$ is generally aspheric. For designs requiring aspheric surfaces, the surface function Z(r) may be given by the general aspheric form:

$$Z(r) = \frac{r^2/r_c}{1 + \sqrt{1 - (1+k)(r/r_c)^2}} + a_4 r^4 + a_6 r^6 \quad \text{Equation 5}$$

where: $r_c$ is the radius of curvature
k is a conic constant
$a_4$ and $a_6$ are higher order aspheric constants For a spherical surface, $k=0$, $a_4=0$, and $a_6=0$. The human cornea may be approximated by $k=-0.16$, $a_4=0$ and $a_6=0$. The radius of curvature, $r_e$, may be specified by the ADD power for correction of presbyopia, and the other parameters may specify corrections for higher-order aberrations.

The above expressions for the thickness profile are intended to be exemplary only. Other mathematical expressions or parameters may be used to describe similar or other thickness profiles. Therefore, the invention is not limited to particular mathematical expressions or parameters for describing the thickness profile.

After the required thickness profile L(r) is determined, the inlay is dimensioned to have substantially the same thickness profile. The profiles should have the same thickness to within about one micron, which would cause a diopter difference of about one eight of a diopter if the center thickness differs by one micron. An eighth of a diopter is half the accuracy with which ophthalmic refractive errors are manually recorded. Next, the thickness profile of the inlay is increased by the finite edge thickness ($h_{edge}$) by the manufacturing process. This finite edge thickness is one factor inducing the drape as illustrated in FIG. 18. When implanted in the cornea, the thickness profile of the inlay is substantially transferred to the anterior corneal surface through the intervening flap, thereby producing the desired post-implant anterior corneal surface in the central region. The draping effect causes the change in the anterior corneal surface thickness to extend beyond the central region. This draping effect can be minimized, e.g., by reducing the finite edge thickness of the inlay as much as possible.

The design method above assumed that the index of refractive of the inlay is the same as the cornea, in which case changes in refractive power of the cornea is due solely to the change in the anterior corneal surface induced by the inlay. An inlay with intrinsic power (e.g., a higher index of refraction than the cornea) may also be used, in which changes in the refractive power is provided by a combination of the physical inlay shape and the intrinsic power (i.e., index of refraction) of the inlay. Design methods for inlays with intrinsic power are described in application Ser. No. 11/381,056, titled "Design of Inlays with Intrinsic Diopter Power," filed on May 1, 2006, the entirety of which is incorporated herein by reference.

For some applications, it is desirable for an inlay to induce an effective optical zone on the anterior corneal surface that is much larger than the inlay diameter. The increase in the effective optical zone allows the inlay to produce a much larger clinical effect on the patient's vision than the actual inlay diameter. In one example, a 1.5 mm-2 mm range diameter inlay has an increased effective optical zone of 4 mm-5 mm, in which the optical effect of the inlay is 2× to 3× greater than its diameter. The increased effective optical zone can also be achieved with inlay diameters outside the above range. For example, the diameter of the inlay may go down to 1 mm or less for some designs, while achieving the desired optical effect.

The increase in the effective optical zone (i.e., "effect" zone) of the inlay can be achieved by increasing the draping effect of the inlay. Increasing the draping effect extends the drape region, and therefore the effective optical zone (i.e., the area of the anterior corneal surface affected by the inlay). The draping effect may be increased, e.g., by increasing the finite edge thickness of the inlay so that the anterior corneal surface returns to its pre-implant surface at a larger radius.

Small diameter inlays inducing effective optical zones much larger than the inlay diameter may be used to correct hyperopia. For example, an inlay with a diameter of 2 mm can provide increased diopter power over an effective optical zone having a diameter of 4 mm. The curvature of the anterior corneal surface in the drape region is greater than the pre-implant anterior corneal surface. Therefore, the draping effect extends the area of the anterior corneal surface where the curvature is increased, thereby extending the effective optical zone of the inlay and providing increased diopter power over a wider diameter than the inlay diameter. This increase in the effective optical zone allows for the correction of hyperopia using smaller diameter inlays.

An inlay with increased effective optical zone may also be used to correct various vision impairments including presbyopia, hyperopia, myopia, and higher order aberrations. In the case of presbyopia, a sufficient "effect" zone may be achieved with an even smaller diameter inlay. For example, a 1 mm diameter inlay may be used to produce a 2 mm diameter "effect" zone.

Figure 20:
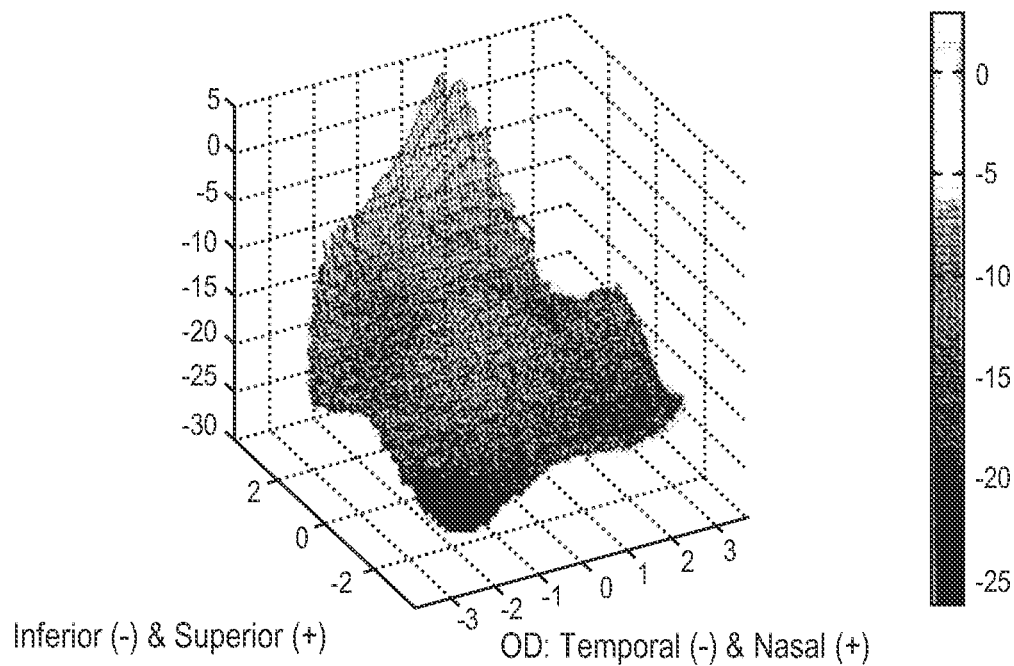
FIG. 20 is a 3D topographic difference map showing the change in the anterior corneal surface induced by an inlay according to an embodiment of the invention.

Clinical data will now be presented in which the effective optical zone induced by an inlay is larger than the inlay diameter. In general, topographic instruments can be used to measure the change in the anterior surface elevation induced by an inlay, calculate the change in the anterior surface curvature and deduce the change in the diopter power. FIG. 20 shows an example of a 3D topographic difference map showing the change in the anterior corneal surface for a subject (subject 1) between a preoperative examination and a one week postoperative examination. In this example, an intracorneal inlay was implanted in subject 1 having a diameter of 2 mm, a center thickness of approximately 36 microns, and an edge thickness of approximately 30 microns. The inlay was placed under a corneal flap created using a laser keratome (by Intralase, Inc.) at a depth of approximately 110 microns. A Scheimpflug topographer ("Pentacam" by Oculus, Inc.) was used to measure the surfaces. From FIG. 20, it is clear that the implanted inlay steepened the anterior corneal surface.

Figure 21:
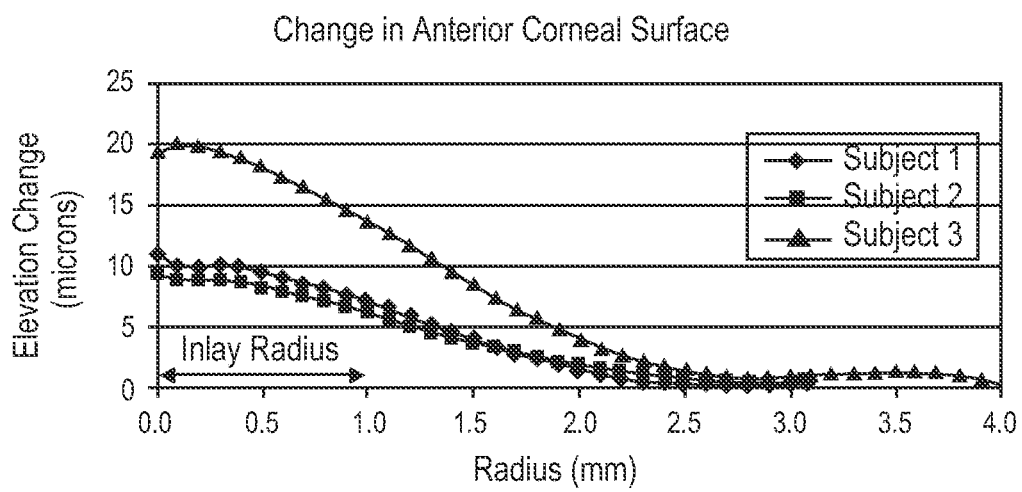
FIG. 21 shows an average radial elevation profile induced by an inlay according to an embodiment of the invention.

FIG. 21 shows the average radial elevation profile calculated from data in FIG. 20. Average radial profiles for two additional subjects (subjects 2 and 3) who received the same inlay design are also shown. Note that the central anterior surface elevation change was less than the center thickness of the inlay. This reflects biomechanical interactions between the inlay material, stromal bed on which it rests and the overlying keratometric flap. However, in all cases the inlay increased the anterior surface elevation beyond the physical diameter of the inlay. FIG. 21 suggests that the effective optical zone induced by the inlay was approximately twice the inlay diameter for this particular design. Inlays with different diameters, center thicknesses and thickness profiles may have different "effect" zone sizes.

Figure 22:
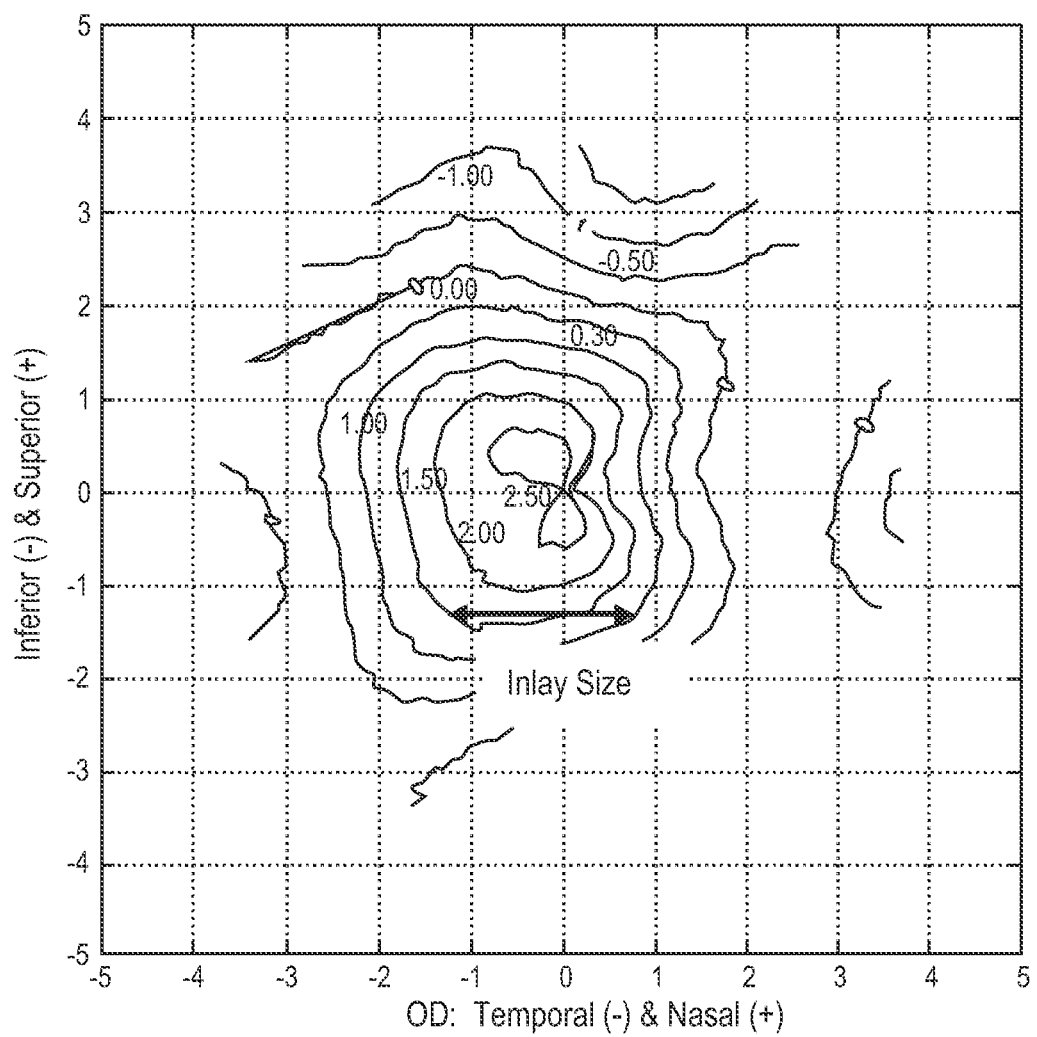
FIG. 22 shows a contour map of the refractive change induced by an inlay according to an embodiment of the invention.

FIG. 22 shows a contour map of the refractive change induced by the intracorneal inlay. This is calculated from the elevation differences by calculating the sagittal curvature map and converting to diopter power using:

$$\text{Diopter power} = (n_c - 1)/\text{sagittal curvature}$$

where $n_c$ is the index of refraction of the cornea. Again, the effective optical zone of the inlay was greater than the diameter of the inlay.

In some embodiments the inlay has a diameter between about 1 mm and about 3 mm, and in some particular embodiments the inlay is about 2 mm in diameter. In some embodiments the inlay central thickness (from anterior to posterior surfaces) is about 20 microns to about 40 microns, while in some particular embodiments the inlay central thickness is about 30 microns, and in some more particular embodiment the central thickness is about 32 microns. In some embodiments the inlay has an edge thickness of about 3 microns to about 16 microns, and in some particular embodiments the edge thickness is about 12 microns. In some embodiments the anterior surface radius of curvature is about 7 mm to about 13 mm, and in some particular embodiments the anterior surface radius of curvature is about 10 mm. In some embodiments the posterior surface radius of curvature is about 5 mm to about 12 mm, and in some particular embodiments the posterior surface radius of curvature is about 8.5 mm.

In one particular embodiment the inlay has a diameter of about 2 mm, the central thickness is about is about 32 microns, the edge thickness is about 12 microns, the anterior surface radius of curvature is about 10 mm, and the posterior surface radius of curvature is about 8.5 mm.

In some embodiments the diameter of the inlay is less than 4 mm.

Exemplary embodiments have been shown and described herein. It will be obvious to those skilled in the art that such embodiments are provided by way of example only. Numerous variations, changes, and substitutions will now occur to those skilled in the art without departing from that which is described herein.

What is claimed is:

1. A method of manufacturing a corneal implant and implanting the corneal implant in an eye, the method comprising:
   manufacturing an implant body to have a meniscus shape, a diameter of approximately 2.5 mm or less, and an index of refraction of 1.376; and
   implanting the implant body in a corneal bed of a cornea;
   wherein implantation of the implant body into the corneal bed causes a change in an anterior surface of the cornea due to the implant body, the change in the anterior surface of the cornea including a central region of increased curvature for near vision and an intermediate region for intermediate vision, while retaining distance vision in a region peripheral to the intermediate region.

2. The method of claim 1, wherein the implant body is implanted below a flap formed in the cornea.

3. The method of claim 2, wherein the flap is repositioned over the implant body after implantation of the implant body in the corneal bed.

* * * * *